(12) United States Patent
Sanghvi et al.

(10) Patent No.: US 6,809,195 B1
(45) Date of Patent: Oct. 26, 2004

(54) PROCESS FOR THE PREPARATION OF OLIGONUCLEOTIDES

(75) Inventors: Yogesh S. Sanghvi, Encinitas, CA (US); Quanlai Song, San Marcos, CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 371 days.

(21) Appl. No.: 09/640,279

(22) Filed: Aug. 16, 2000

(51) Int. Cl.[7] .......................... C07H 21/00; C12P 19/34

(52) U.S. Cl. .................. 536/25.3; 536/23.1; 536/25.31; 536/25.32; 536/25.33; 435/91.1

(58) Field of Search .......................... 536/25.31, 25.32, 536/25.33, 22.1, 23.1, 24.5, 25.3; 435/91.1, 6, 130; 585/833

(56) References Cited

U.S. PATENT DOCUMENTS

| | | | |
|---|---|---|---|
| 4,458,066 A | * | 7/1984 | Caruthers |
| 4,816,571 A | | 3/1989 | Andrus et al. |
| 5,149,798 A | * | 9/1992 | Agrawal et al. ............ 536/25.3 |
| 5,166,387 A | * | 11/1992 | Hirschbein |
| 5,386,023 A | | 1/1995 | Sanghvi et al. |
| 5,424,184 A | * | 6/1995 | Santamaria |
| 5,614,621 A | * | 3/1997 | Ravikumar |
| 5,750,666 A | * | 5/1998 | Caruthers |
| 5,859,221 A | | 1/1999 | Cook et al. |
| 6,025,482 A | | 2/2000 | Cook et al. |
| 6,399,765 B1 | * | 6/2002 | Krotz |

FOREIGN PATENT DOCUMENTS

WO     WO 93/07883     4/1993

OTHER PUBLICATIONS

Zhang, Z., et al., "Solid phase synthesis of oligonucleotide phosphorothioate analogues using bis(ethoxythiocarbonyl)tetrasulfide as a new sulfur–transfer reagent." *Tetrajedron Lett.*, 1998, 39, 2467–2470.

Zhang, Z., et al., "Solid phase synthesis of oligonucleotide phosphorothioate analogues using 3–methyl–1,2, 4–dithiazolin–5–one (MEDITH) as a new sulfur–transfer reagent." *Tetrahedron Lett.*, 1999, 40, 2095–2098.

Polushin, N. N. et al., "Synthesis of Oligonucleotides Containing 2'–Azido–and 2'–Amino–2'–deoxyuridine Using Phosphotriester Chemistry," *Tetrahedron Letts.*, 1996, 37(19), 3227–3230.

Rao, M. V., et al., "Solid phase synthesis of phosphorothioate oligonucleotides using benzyltriethylammonium tetrathiomolybdate as a rapid sulfur transfer reagent," *Tetrahedron Lett.*, 1994, 35(36), 6741–6744.

Rao, M. V. et al., "Dibenzoyl Tetrasulphide–A Rapid Sulphur Transfer Agent in the Synthesis of Phosphorothioate Analogues of Oligonucleotides", *Tetrahedron Letts.*, 1992, 33, 4839–4842.

Roelen, H. et al., "A study on the use of phenylacetyl disulfide in the solid–phase synthesis of oligodeoxynucleoside phosphorothioates," *Recl. Trav. Chim. Pays–Bas*, 1991, 110, 325–331.

Stec, W.J. et al., "Bis (O,O–Diisopropoxy Phosphinothioyl) Disulfide—A Highly Efficient Sulfurizing Reagent for Cost-–Effective Synthesis of Oligo(Nucleoside Phosphorothioate)s", *Tetrahedron Letts.*, 1993, 34(33), 5317–5320.

Tang, J., et al., "Large–scale synthesis of oligonucleotide phosphorothioates using 3–amino–1,2, 4–dithiazole–5–thione as an efficient sulfur–transfer reagent." *Organic Proc. Res. & Dev.*, 2000, 4, 194–198.

Vu, H., et al., "Internucleotide phosphite sulfurization with tetraethylthiuram disulfide. Phosphorothioate oligonucleotides synthesis via phosphoramidite chemistry," *Tetrahedron Lett.*, 1991, 32(26), 3005–3008.

Xu, Q. et al., "Use of 1,2,4–dithiazolidine (DtsNH) and 3–ethoxy–1,2,4–dithiazoline–5–one (EDITH) for synthesis of phosphorothioate–containing oligodeoxyribonucleotides", *Nucl. Acids Res.*, 1996, 24(9), 1602–1607.

Xu, Q. et al., "Efficient introduction of phosphorothioates into RNA oligonucleotides by 3–ethoxy–1,2, 4–dithiazoline–5–one (EDITH)". *Nucl. Acids Res.*, 1996, 24, 3643–3644.

Beaucage, S.L. et al., "The Synthesis of Modified Oligonucleotides by the Phosphoramidite Approach and their Applications", *Tetrahedron*, 1993, 49, 6123–6194.

Cheruvallah, Z.S., et al., "Synthesis of antisense oligonucleotides: Replacement of 3H–1,2–benzodithiol–3–one 1, 1–dioxide (Beaucage Reagent) with phenylacetyl disulfide (PADS) as efficient sulfurization reagent: From bench to bulk manufacture of active pharmaceutical ingredient," *Organic Process Research & Development*, 2000, 4, 199–204.

Cummings, A.D., et al., "Some observations with ultra–accelerators," *Ind. Eng. Chem.*, 1928, 20(11), 1173–1176.

Delgardo, C., et al., "The uses and properties of PEG–linked proteins," *Critical Reviews in Therapeutic Drug Carrier Systems*, 1992, 9(3,4), 249–304.

Efimov, V.A. et al., "New efficient sulfurizing reagents for the preparation of oligodeoxyribonucleotide phosphorothioate analogues", *Nucl. Acids Res.*, 1995, 23, 4029–4033.

(List continued on next page.)

*Primary Examiner*—Sean McGarry
*Assistant Examiner*—Janet L. Epps-Ford
(74) *Attorney, Agent, or Firm*—Woodcock Washburn LLP

(57) ABSTRACT

The present invention discloses methods for synthesizing oligomeric compounds. The methods include a modified phosphoramidite protocol wherein the oxidation and capping steps are combined into a single step. The methods result in increased efficiency and are especially amenable to the large scale synthesis of oligomeric compounds.

40 Claims, No Drawings-

OTHER PUBLICATIONS

Eleueri, A., et al., "Pyridinium trifluoroacetate/N-methylimidazole as an efficient activator for oligonucleotide synthesis via the phosphoramidite method," *Organic Process Res. & Dev.,* 2000, 4, 182–189.

Eliel, E.L., et al., "Highly stereoselective syntheses involving N-alkyl-4,4,7α-trimethyl-trans-octahydro-1,3-benzoxazine intermediates," *J. Org. Chem.,* 1990, 55(7), 2114–2119.

He, X-C. et al., "Highly Enantioselective Syntheses of α-Hydroxyacids Using N-Benzyl-4,4,7α-Trimethyl-Trans-Octahydro-1,3-Benzoxazine as a Chiral Adjuvant," *Tetrahedron,* 1987, 43(21), 4979–4987.

Iyer, R.P. et al., "3H-1,2-Benzodithiole-3-one 1,1-Dioxide as an Improved Sulfurizing Reagent in the Solid-Phase Synthesis of Oligodeoxyribonucleoside Phosphorothioates", *J. Am. Chem. Soc.,* 1990, 112, 1253–1254.

Iyer, R.P. et al., "The Automated Synthesis of Sulfur-Containing Oligodeoxyribonucleotides Using 3H-1,2-Benzodithiol-3-one 1,1-Dioxide as a Sulfur-Transfer Reagent", *J. Org. Chem.,* 1990, 55, 4693–4699.

Kamer, P.C.J. et al., "An Efficient Approach Toward the Synthesis of Phosphorothioate Diesters via the Schonberg Reaction", *Tetrahedron Letts.,* 1989, 30, 6757–6760.

* cited by examiner

SEQUENCE LISTING

<160> NUMBER OF SEQ ID NOS: 1

<210> SEQ ID NO 1
<211> LENGTH: 20
<212> TYPE: DNA
<213> ORGANISM: Artificial Sequence
<220> FEATURE:
<223> OTHER INFORMATION: Novel Sequence

<400> SEQUENCE: 1
gtgctcatgg tgcacggtct                                                 20

PROCESS FOR THE PREPARATION OF OLIGONUCLEOTIDES

FIELD OF THE INVENTION

The present invention is directed to methods for synthesizing oligonucleotides and analogs thereof. In one aspect of the invention the methods combine oxidation and capping into a single step to improve the efficiency of synthesis. The overall synthesis preferably is completed in less time with a reduction in bulk reagents required. More specific objectives and advantages of the invention will hereinafter be made clear or become apparent to those skilled in the art during the course of explanation of preferred embodiments of the invention.

BACKGROUND OF THE INVENTION

Modified oligonucleotides are of great value in molecular biological research and in applications such as anti-viral therapy. Modified oligonucleotides which can block RNA translation, and are nuclease resistant, are useful as antisense reagents. In addition to oligonucleotides that have phosphodiester internucleotide linkages, sulfurized oligonucleotides which contain, for example, phosphorothioate linkages are also of interest in these areas. Because of their chirality (Rp and Sp) phosphorothioate containing oligonucleotides are useful in determining stereochemical pathways of certain enzymes which recognize nucleic acids.

It is well known that most of the bodily states in multicellular organisms, including most disease states, are effected by proteins. Such proteins, either acting directly or through their enzymatic or other function, contribute in major proportion to many diseases and regulatory functions in animals and humans. For disease states, classical therapeutics has generally focused upon interactions with such proteins in efforts to moderate their disease-causing or disease-potentiating functions. In newer therapeutic approaches, modulation of the actual production of such proteins is desired. By interfering with the production of proteins, the maximum therapeutic effect may be obtained with minimal side effects. It is therefore a general object of such therapeutic approaches to interfere with or otherwise modulate gene expression, which would lead to undesired protein formation.

One method for inhibiting specific gene expression is with the use of oligonucleotides, especially oligonucleotides which are complementary to a specific target messenger RNA (mRNA) sequence. Several oligonucleotides are currently undergoing clinical trials for such use. Phosphorothioate oligonucleotides are presently being used as such antisense agents in human clinical trials for various disease states, including use as antiviral agents.

Transcription factors interact with double-stranded DNA during regulation of transcription. Oligonucleotides can serve as competitive inhibitors of transcription factors to modulate their action. Several recent reports describe such interactions (see Bielinska, A., et. al., Science, 1990, 250, 997–1000; and Wu, H., et. al., Gene, 1990, 89, 203–209).

In addition to such use as both indirect and direct regulators of proteins, oligonucleotides and their analogs also have found use in diagnostic tests. Such diagnostic tests can be performed using biological fluids, tissues, intact cells or isolated cellular components. As with gene expression inhibition, diagnostic applications utilize the ability of oligonucleotides and their analogs to hybridize with a complementary strand of nucleic acid. Hybridization is the sequence specific hydrogen bonding of oligomeric compounds via Watson-Crick and/or Hoogsteen base pairs to RNA or DNA. The bases of such base pairs are said to be complementary to one another.

Oligonucleotides and their analogs are also widely used as research reagents. They are useful for understanding the function of many other biological molecules as well as in the preparation of other biological molecules. For example, the use of oligonucleotides and their analogs as primers in PCR reactions has given rise to an expanding commercial industry. PCR has become a mainstay of commercial and research laboratories, and applications of PCR have multiplied. For example, PCR technology now finds use in the fields of forensics, paleontology, evolutionary studies and genetic counseling. Commercialization has led to the development of kits which assist non-molecular biology-trained personnel in applying PCR. Oligonucleotides and their analogs, both natural and synthetic, are employed as primers in such PCR technology.

Oligonucleotides and their analogs are also used in other laboratory procedures. Several of these uses are described in common laboratory manuals such as *Molecular Cloning, A Laboratory Manual*, Second Ed., J. Sambrook, et al., Eds., Cold Spring Harbor Laboratory Press, 1989; and *Current Protocols In Molecular Biology*, F. M. Ausubel, et al., Eds., Current Publications, 1993. Such uses include as synthetic oligonucleotide probes, in screening expression libraries with antibodies and oligomeric compounds, DNA sequencing, in vitro amplification of DNA by the polymerase chain reaction, and in site-directed mutagenesis of cloned DNA. See Book 2 of *Molecular Cloning, A Laboratory Manual*, supra. See also "DNA-protein interactions and The Polymerase Chain Reaction" in Vol. 2 of *Current Protocols In Molecular Biology*, supra.

Oligonucleotides and their analogs can be synthesized to have customized properties that can be tailored for desired uses. Thus a number of chemical modifications have been introduced into oligomers to increase their usefulness in diagnostics, as research reagents and as therapeutic entities. Such modifications include those designed to increase binding to a target strand (i.e. increase their melting temperatures, Tm), to assist in identification of the oligonucleotide or an oligonucleotide-target complex, to increase cell penetration, to stabilize against nucleases and other enzymes that degrade or interfere with the structure or activity of the oligonucleotides and their analogs, to provide a mode of disruption (terminating event) once sequence-specifically bound to a target, and to improve the pharmacokinetic properties of the oligonucleotide.

The synthesis of oligonucleotides has classically involved obtaining a desired product on a small scale. The synthesis of oligonucleotides has more recently evolved to the point that routine syntheses are being performed on kilogram scale. Moving forward the next step is the synthesis of oligonucleotides and analogs on ton scale to supply large quantities to meet demands for ongoing pharmaceutical sales and clinical trials. The evolution of oligonucleotide synthetic techniques toward larger scale is requiring a reevaluation of each aspect of the synthetic process. There is an ongoing need in the art of oligomer synthesis to improve the efficiency of synthesis.

The chemical literature discloses numerous protocols for coupling nucleosides through phosphorous-containing covalent linkages to produce oligonucleotides of defined sequence. One of the most routinely used protocols is the phosphoramidite protocol (see, e.g, Advances in the Synthesis of Oligonucleotides by the Phosphoramidite Approach, Beaucage, S. L.; Iyer, R. P., Tetrahedron, 1992, 48, 2223–2311 and references cited therein; and The synthesis of Modified Oligonucleotides by the Phosphoramidite Approach and their applications, Beaucage, S. L.; Iyer, R. P., Tetrahedron, 1993, 49, 6123–6194 and references cited therein), wherein a nucleoside or oligonucleotide having a free hydroxyl group is reacted with a protected phosphoramidite monomer in the presence of a weak acid to form a phosphite-linked structure. Oxidation of the phosphite linkage with a suitable reagent effects conversion of a $P^{III}$ internucleoside linkage to a $P^V$ internucleoside linkage. For the purpose of this application, such reagents include oxygen transfer reagents and sulfur transfer reagents. Subsequent hydrolysis of the cyanoethyl group yields the desired phosphodiester or phosphorothioate linkage.

Phosphoramidites are commercially available from a variety of commercial sources (included are: Glen Research, Sterling, Va.; Amersham Pharmacia Biotech Inc., Piscataway, N.J.; Cruachem Inc., Aston, Pa.; Chemgenes Corporation, Waltham, Mass.; Proligo LLC, Boulder, Colo.; PE Biosystems, Foster City Calif.; Beckman Coulter Inc., Fullerton, Calif.).

An efficient sulfur transfer reagent is important to the success of obtaining high quality phosphorothioate product with a low percentage of phosphate linkages. A number of sulfur transfer reagents have been reported, including Beaucage reagent, 3-ethoxy-1,2,4-dithiozloine-5-one (EDITH), 1,2,4-dithiozoline-3,5-dione, 3-methyl-ethoxy-1,2,4-dithiozloine-5-one (MEDITH), phenylacetyl disulfide (PADS), tetraethylthiuram disulfide (TETD) and others. The cost of sulfur transfer reagents and their efficiency has to be taken into account when performing large-scale manufacturing. Beaucage reagent is expensive (about $5.00 per gram) and is being replaced by other cheaper reagents like PADS. PADS was first introduced by van Boom but did not show adequate sulfur transfer efficiency under the original conditions, which did not use a base during the sulfurization step (Roclen et al., Recl. Trav. Chim. Pays-Bas, 1991, 110, 325–331).

The use of elemental sulfur in olignucleotide synthesis presents problems and is not suitable for automation because of sulfur's insolubility in most organic solvents. Furthermore, carbon disulfide, a preferred source of sulfur, has undesirable volatility and an undesirably low flash point. Unwanted side products are often observed with the use of dibenzoyl tetrasulfide. Beaucage reagent, while a relatively efficient sulfurization reagent, is difficult to synthesize and not particularly stable. Furthermore, use of Beaucage reagent forms a secondary reaction product which is a potent oxidizing agent. (R. P. Iyer et al., J. Am. Chem. Soc. 112, pp. 1253–1254 (1990); R. P. Iyer et al., J. Org. Chem. 55, 4693–4699 (1990)). This can further lead to unwanted side products which can be difficult to separate from the desired reaction product. Tetraethylthiuram disulfide while relatively inexpensive and stable, has a sulfurization reaction rate which can be undesirable slow.

A method of preparing phosphorothioate oligonucleotides using tetraethylthiuram disulfide is disclosed in U.S. Pat. No. 5,166,387. Although the use of tetraethylthiuram disulfide as a sulfur transfer reagent has been described since 1992, it has not been used for commercial scale production of phosphorothioate oligonucleotides. Beaucage reagent and phenylacetyl disulfide (PADS) are the only reagents that have been used commercially with good results. Our experiments with tetraethylthiuram disulfide indicate that there is a significant amount of side product formation (see Example 8) along with the desired phosphorothioate product. Although we do not wish to be bound by theory it is believed that tetraethylthiuram disulfide is an overly stable sulfur transfer reagent that is difficult to dissociate after reaction with the $P^{III}$ species.

Thus, there remains a need for improved methods and reagents for preparing oligomeric compounds. The present invention is directed to these, as well as other, important ends.

SUMMARY OF THE INVENTION

The present invention provides methods of preparing oligomeric compounds having at least one moiety of formula:

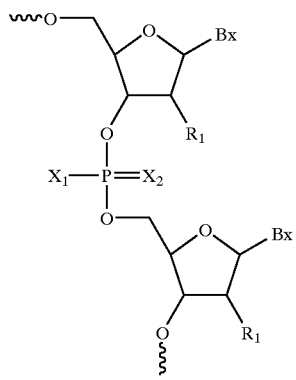

wherein:
$X_2$ is O or S;
$X_1$ is Pg—O—, Pg—S—, $C_1$–$C_{10}$ straight or branched chain alkyl, $CH_3(CH_2)_{nn}$—O—, $R_2R_3N$— or a group remaining from coupling a chiral auxiliary;.
nn is from 0 to 10;
Pg is $CH_3$, —$CH_2CH_2CN$, —$C(CH_3)$ $(CH_3)$—$CCl_3$, —$CH_2$-$CCl_3$, —$CH_2CH$=$CH_2$, $CH_2CH_2SiCH_3$, 2-yl-ethyl phenylsulfonate, δ-cyano-butenyl, cyano p-xylyl, diphenylsilylethyl, 4-nitro-2-yl-ethylbenzene, 2-yl-ethyl-methyl sulfonate, methyl-N-trifluoroacetyl ethyl, acetoxy phenoxy ethyl, or a blocking group;
each $R_2$ and $R_3$ is, independently, hydrogen, $C_1$–$C_{10}$ alkyl, cycloalkyl or aryl;
or optionally, $R_2$ and $R_3$, together with the nitrogen atom to which they are attached form a cyclic moiety that may include an additional heteroatom selected from O, S and N;
each Bx is, independently, a heterocyclic base moiety; and
each $R_1$ is, independently, H, a blocked hydroxyl group, or a sugar substituent group; comprising the steps of:
(a) providing a 5'-O-protected compound of the formula:

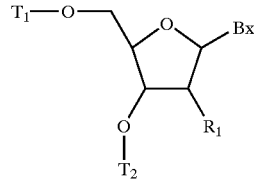

wherein:
$T_1$ is a hydroxyl protecting group; and
$T_2$ is a covalent attachment to a support media, a nucleoside bound to a support media, a nucleotide, an oligonucleoside or an oligonucleotide;
(b) treating said 5'-O-protected compound with a deprotecting reagent for a time and under conditions effective to form a 5'-O-deprotected compound;

(c) coupling said 5'-O-deprotected compound with an activated phosphorus composition of the formula:

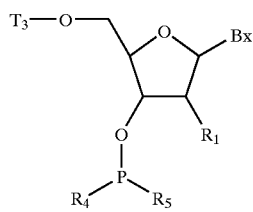

wherein:

$T_3$ is a hydroxyl protecting group, a nucleoside, a nucleotide, an oligonucleoside or an oligonucleotide;

$R_4$ is $N(L_1)L_2$;

each $L_1$ and $L_2$ is, independently, $C_{1-6}$ straight or branched alkyl, or a $C_{5-7}$ cyclic aliphatic ring system;

or $L_1$ and $L_2$ are joined together to form a 4- to 13-membered heterocyclic ring system including the nitrogen atom to which $L_1$ and $L_2$ are attached, wherein said ring system optionally includes at least one additional heteroatom selected from O, N and S; and $R_5$ is $X_1$;

or $R_4$ and $R_5$ together with the phosphorus atom to which $R_4$ and $R_5$ are attached form a chiral auxiliary;

for a time and under conditions effective to form an extended compound having the formula:

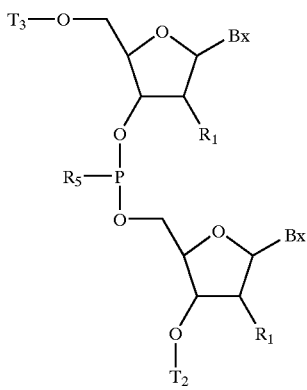

(d) treating said extended compound with a mixture comprising an oxidizing reagent and a capping reagent for a time and under conditions effective to form said oligomeric compound.

The methods can include further treatment of the oligomeric compound with a reagent for a time and under conditions effective to remove the blocking groups, thereby forming a deblocked oligomeric compound. This reagent can also be effective to cleave the oligomeric compound from the support media. One such reagent is aqueous ammonium hydroxide. Alternatively, the deblocking can be effected with one reagent, and a further reagent can effect cleavage from the support media. Also included is treatment with a deprotecting reagent for a time and under conditions effective to deprotect the $T_3$ hydroxyl protecting group.

In one embodiment of the invention, the mixture comprises from 0.02M to 0.2M oxidizing reagent with a preferred range is from 0.1M to 0.2M.

The oxidizing reagent can be one that transfers an oxygen atom. Effective oxidizing reagents for oxygen transfer are iodine, m-chloroperbenzoic acid, iodobenzene diacetate, tetra-n-butylammonium periodate, tert-butyl hydroperoxide, di-tert-butyl hydroperoxide, cumene hydroperoxide, hydrogen peroxide; bis-trimethylsilyl peroxide; dinitrogen tetroxide, oxone, molecular oxygen, (1S)-(+)-(10-camphorsulfonyl)oxaziridine or a peracid with iodine, m-chloroperbenzoic acid, iodobenzene diacetate, tert-butyl hydroperoxide, di-tert-butyl hydroperoxide, hydrogen peroxide; oxone, molecular oxygen or a peracid being preferred.

The oxidizing reagent can also be one that transfers a sulfur atom. Effective oxidizing reagents for sulfur transfer are 3-amino-1,2,4-dithiazole-5-thione; 3-ethoxy-1,2,4-dithiazoline-5-one; 1,2,4-dithiazolidine-3,5-dione; 3-methyl-1,2,4-dithiazolin-5-one; or dimethylthiuram disulfide with dimethylthiuram disulfide being preferred.

In one embodiment, the capping reagent is prepared by mixing equal volumes of two components prior to the capping step. The first component is a mixture of an acylating agent such as N-methylimidazole or 4-dimethylaminopyridine and a base such as pyridine or 2,6-lutidine in acetonitrile or tetrahydrofuran. The second component is a solution of an acid anhydride such as acetic anhydride, chloroacetic anhydride, t-butylphenoxyacetic anhydride in acetonitrile or tetrahydrofuran.

One preferred capping reagent comprises about equal volumes of a first component containing from 5% to about 25% N-methylimidazole, from about 20% to about 50% pyridine and from about 20% to about 50% acetonitrile, added to a second component containing from about 20% to about 50% acetic anhydride in acetonitrile.

Another preferred capping reagent comprises about equal volumes of a first component containing about 5% to about 25% 4-dimethylaminopyridine, from about 20% to about 50% 2,6-lutidine in acetonitrile, added to a second component containing from about 20% to about 50% acetic anhydride in acetonitrile.

The mixture of oxidizing reagent and capping reagent can comprise, for example, dimethylthiuram disulfide, acetic anhydride, acetonitrile, N-methyl imidazole, or pyridine. A preferred mixture comprises from about 0.05M to 0.2M dimethylthiuram disulfide, about 10% acetic anhydride, about 10% N-methyl imidazole and about 15% pyridine in a suitable solvent. Suitable solvents include acetonitrile, toluene, ethyl acetate, tetrahydrofuran, dichloromethane, dichloroethane, dioxane, dimethylacetamide and dimethylformamide.

In another embodiment of the invention the coupling of the 5'-O-deprotected compound with the activated phosphorus composition is performed in the presence of an activating agent that renders the phosphorous atom more susceptible to nucleophilic attack. Preferred activating agents include 1-H-tetrazole and 4,5-dicyanoimidazole.

Exemplary cyclic moieties according to the invention include morpholino or phthalimido moieties.

Each $L_1$ and $L_2$ can be, independently, $C_{1-6}$ alkyl with isopropyl being a preferred alkyl group for $L_1$ and $L_2$. $L_1$ and $L_2$ can also be joined together to form a heterocyclic ring system including the nitrogen atom to which said $L_1$ and $L_2$ are attached, the ring system optionally includes at least one additional heteroatom selected from O, N and S. A preferred heterocyclic ring system is morpholino.

Representative substituent groups according to the invention include, $C_1$–$C_{20}$ alkyl, $C_2$–$C_{20}$ alkenyl, $C_2$–$C_{20}$ alkynyl, $C_5$–$C_{20}$ aryl, O-alkyl, O-alkenyl, O-alkynyl, O-aryl, O-aralkyl, O-alkylamino, O-alkylaminoalkyl (O-alkyl-N(H) alkyl), O-alkylaminodialkyl (O-alkyl-N-(alkyl)$_2$), O-alkylalkoxy (O-alkyl-O-alkyl), O-alkyl-(N-imidazole), thiol, S-alkyl, S-alkenyl, S-alkynyl, NH-alkyl, NH-alkenyl, NH-alkynyl, N-dialkyl, S-aryl, NH-aryl, S-aralkyl, NH-aralkyl, N-phthalimido, halogen keto, carboxyl, nitro, nitroso, nitrile, trifluoromethyl, trifluoromethoxy, N-imidazole, azido, hydrazino, hydroxylamino, isocyanato, sulfoxide, sulfone, sulfide, disulfide, silyl, heterocycle, carbocycle, polyamine, polyamide, polyalkylene glycol, or polyether;

Alternatively, one or more substituent groups has one of formula I or II:

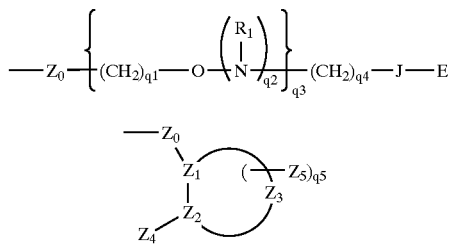

wherein:

$Z_0$ is O, S or NH;

J is a single bond, O or C(=O);

E is $C_1–C_{10}$ alkyl, $N(R_1)(R_2)$, $N(R_1)(R_5)$, $N=C(R_1)(R_2)$, $N=C(R_1)(R_5)$ or has one of formula III or IV;

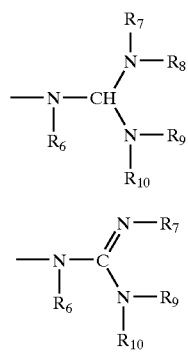

each $R_6$, $R_7$, $R_8$, $R_9$ and $R_{10}$ is, independently, hydrogen, $C(O)R_{11}$, substituted or unsubstituted $C_2–C_{10}$ alkyl, substituted or unsubstituted $C_2–C_{10}$ alkenyl, substituted or unsubstituted $C_2–C_{10}$ alkynyl, alkylsulfonyl, arylsulfonyl, a chemical functional group or a conjugate group, wherein the substituent groups are selected from hydroxyl, amino, alkoxy, carboxy, benzyl, phenyl, nitro, thiol, thioalkoxy, halogen, alkyl, aryl, alkenyl and alkynyl;

or optionally, $R_7$ and $R_8$, together form a phthalimido moiety with the nitrogen atom to which they are attached;

or optionally, $R_9$ and $R_{10}$, together form a phthalimido moiety with the nitrogen atom to which they are attached;

each $R_{11}$ is, independently, substituted or unsubstituted $C_1–C_{10}$ alkyl, trifluoromethyl, cyanoethyloxy, methoxy, ethoxy, t-butoxy, allyloxy, 9-fluorenylmethoxy, 2-(trimethylsilyl)-ethoxy, 2,2,2-trichloroethoxy, benzyloxy, butyryl, isobutyryl, phenyl or aryl;

$R_5$ is T-L,

T is a bond or a linking moiety;

L is a chemical functional group, a conjugate group or a support media;

each $R_1$ and $R_2$ is, independently, H, a nitrogen protecting group, substituted or unsubstituted $C_1–C_{10}$ alkyl, substituted or unsubstituted $C_2–C_{10}$ alkenyl, substituted or unsubstituted $C_2–C_{10}$ alkynyl, wherein said substitution is $OR_3$, $SR_3$, $NH_3^+$, $N(R_3)(R_4)$, guanidino or acyl where said acyl is an acid amide or an ester;

or $R_1$ and $R_2$, together, are a nitrogen protecting group or are joined in a ring structure that optionally includes an additional heteroatom selected from N and O;

or $R_1$, T and L, together, are a chemical functional group;

each $R_3$ and $R_4$ is, independently, H, $C_1–C_{10}$ alkyl, a nitrogen protecting group, or $R_3$ and $R_4$, together, are a nitrogen protecting group;

or $R_3$ and $R_4$ are joined in a ring structure that optionally includes an additional heteroatom selected from N and O;

$Z_4$ is OX, SX, or $N(X)_2$;

each X is, independently, H, $C_1–C_8$ alkyl, $C_1–C_8$ haloalkyl, $C(=NH)N(H)R_5$, $C(=O)N(H)R_5$ or $OC(=O)N(H)R_5$;

$R_5$ is H or $C_1–C_8$ alkyl;

$Z_1$, $Z_2$ and $Z_3$ comprise a ring system having from about 4 to about 7 carbon atoms or having from about 3 to about 6 carbon atoms and 1 or 2 hetero atoms wherein said hetero atoms are selected from oxygen, nitrogen and sulfur and wherein said ring system is aliphatic, unsaturated aliphatic, aromatic, or saturated or unsaturated heterocyclic;

$Z_5$ is alkyl or haloalkyl having 1 to about 10 carbon atoms, alkenyl having 2 to about 10 carbon atoms, alkynyl having 2 to about 10 carbon atoms, aryl having 6 to about 14 carbon atoms, $N(R_1)(R_2)$ $OR_1$, halo, $SR_1$ or CN;

each $q_1$ is, independently, an integer from 1 to 10;

each $q_2$ is, independently, 0 or 1;

$q_3$ is 0 or an integer from 1 to 10;

$q_4$ is an integer from 1 to 10;

$q_5$ is from 0, 1 or 2; and provided that when $q_3$ is 0, $q_4$ is greater than 1.

In one embodiment of the present invention $X_1$ is Pg—O—, Pg—S—, —$CH_3$, $CH_3$—O—, morpholino or —$NR_2R_3$ where each $R_2$ and $R_3$ is, independently, hydrogen or $C_1–C_{10}$ alkyl. Where Pg is $CH_2CH_2CN$, diphenylsilylethyl, δ-cyanobutenyl, cyano p-xylyl, methyl-N-trifluoroacetyl ethyl or acetoxy phenoxy ethyl.

Representative heterocyclic bases include adenine, $N^6$-benzoyladenine, cytosine, $N^4$-benzoylcytosine, 5-methylcytosine, $N^4$-benzoyl-5-methylcytosine, thymine, uracil, guanine, $N^2$-isobutyrylguanine and 2-aminoadenine, as well as protected (or "blocked") forms thereof.

In certain embodiments of the present invention, the support media bound nucleoside, nucleotide, oligonucleoside or oligonucleotide is blocked at reactive sites. In one embodiment the blocking groups are acid stable. In another embodiment the blocking groups are base labile.

Deprotecting reagents can be acidic, neutral or basic. Preferred deprotecting reagents are dichloroacetic acid, trichloroacetic acid, zinc bromide, $AlCl_3$, $TiCl_4$, (Et)AlCl, (I-Bu)$_2$AlCl, ceric ammonium nitrate, 1,1,1,3,3,3-hexafluoro-2-propanol, and diethyloxomalonate. A particularly preferred deprotecting reagent is 2-5% dichloroacetic acid in dichloromethane or dichloroethane. In a further embodiment the deprotecting reagent is a fluoride moiety where a preferred fluoride moiety is $BF_3$-etherate.

The oligomeric compounds of the invention typically comprises from 5 to about 50 nucleosides, with from 8 to about 30 nucleosides being preferred and from 15 to about 25 nucleosides being more preferred.

The present invention also provides methods for the preparation of oligomeric compounds having at least one moiety of formula:

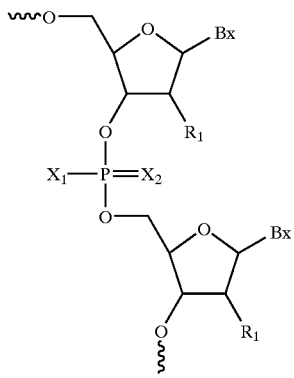

wherein:

$X_1$ is Pg—O—, Pg—S—, $C_1$–$C_{10}$ straight or branched chain alkyl, $CH_3(CH_2)_{nn}$—O—, $R_2R_3N$— or a group remaining from coupling a chiral auxiliary;

nn is from 0 to 10;

Pg is $CH_3$, —$CH_2CH_2CN$, —$C(CH_3)$ $(CH_3)$—$CCl_3$, —$CH_2$—$CCl_3$, —$CH_2CH=CH_2$, $CH_2CH_2SiCH_3$, 2-yl-ethyl phenylsulfonate, δ-cyanobutenyl, cyano p-xylyl, diphenylsilylethyl, 4-nitro-2-yl-ethylbenzene, 2-yl-ethyl-methyl sulfonate, methyl-N-trifluoroacetyl ethyl, acetoxy phenoxy ethyl, or a blocking group;

each $R_2$ and $R_3$ is, independently, hydrogen, $C_1$–$C_{10}$ alkyl, cycloalkyl or aryl;

or optionally, $R_2$ and $R_3$, together with the nitrogen atom to which they are attached form a cyclic moiety that may include an additional heteroatom selected from O, S and N;

each Bx is, independently, a heterocyclic base moiety or a blocked heterocyclic base moiety; and each $R_1$ is, independently, H, a blocked hydroxyl group, a sugar substituent group or a blocked sugar substituent group; comprising the steps of:

(a) providing a 5'-O-protected compound of the formula:

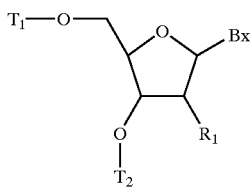

wherein:

$T_1$ is a hydroxyl protecting group; and $T_2$ is a covalent attachment to a support media, or a support media bound nucleoside, nucleotide, oligonucleoside or oligonucleotide;

(b) treating said 5'-O-protected compound with a deprotecting reagent for a time and under conditions effective to form a 5'-O-deprotected compound;

(c) coupling said 5'-O-deprotected compound with an activated phosphorus composition of the formula:

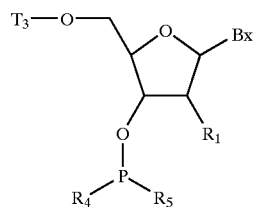

wherein:

$T_3$ is a hydroxyl protecting group, a nucleoside, a nucleotide, an oligonucleoside or an oligonucleotide;

$R_4$ is $N(L_1)L_2$;

each $L_1$ and $L_2$ is, independently, $C_{1-6}$ straight or branched alkyl, or a $C_{5-7}$ cyclic aliphatic ring system;

or $L_1$ and $L_2$ are joined together to form a 4- to 13-membered heterocyclic ring system including the nitrogen atom to which $L_1$ and $L_2$ are attached, wherein said ring system optionally includes at least one additional heteroatom selected from O, N and S; and $R_5$ is $X_1$;

or $R_4$ and $R_5$ together with the phosphorus atom to which $R_4$ and $R_5$ are attached form a chiral auxiliary;

for a time and under conditions effective to form an extended compound having the formula:

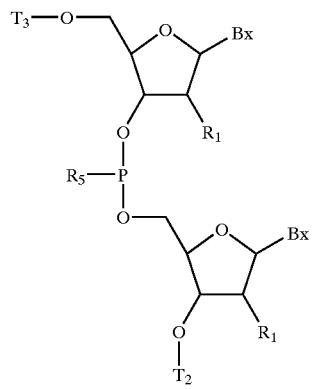

(d) treating said extended compound with dimethylthiuram disulfide in a solvent thereby forming a sulfurized compound having the formula:

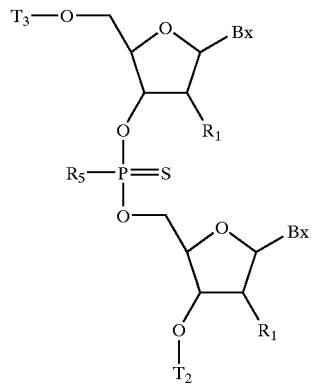

(e) treating said sulfurized compound with a capping reagent for a time and under conditions effective to form said oligomeric compound.

In one embodiment the dimethylthiuram disulfide is from about 0.02M to about 0.2M in said solvent. In a preferred embodiment the dimethylthiuram disulfide is from about 0.1M to about 0.2M in said solvent.

The present invention also provides methods of preparing oligomeric compounds having at least one moiety having one of the formulas:

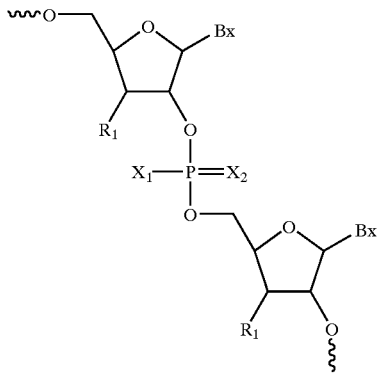

or

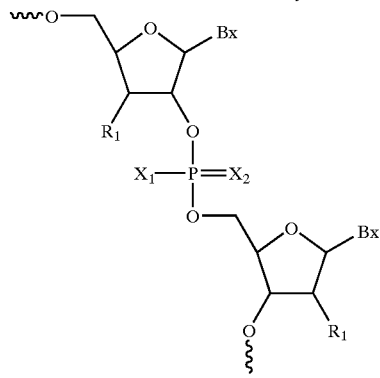

wherein:

$X_2$ is O or S;

$X_1$ is Pg—O—, Pg—S—, $C_1$–$C_{10}$ straight or branched chain alkyl, $CH_3(CH_2)_{nn}$—O—, $R_2R_3N$— or a group remaining from coupling a chiral auxiliary;

nn is from 0 to 10;

Pg is $CH_3$, —$CH_2CH_2CN$, —$C(CH_3)(CH_3)$—$CCl_3$, —$CH_2$—$CCl_3$, —$CH_2CH$=$CH_2$, $CH_2CH_2SiCH_3$, 2-yl-ethyl phenylsulfonate, δ-cyanobutenyl, cyano p-xylyl, diphenylsilylethyl, 4-nitro-2-yl-ethylbenzene, 2-yl-ethyl-methyl sulfonate, methyl-N-trifluoroacetyl ethyl, acetoxy phenoxy ethyl, or a blocking group;

each $R_2$ and $R_3$ is, independently, hydrogen, $C_1$–$C_{10}$ alkyl, cycloalkyl or aryl;

or optionally, $R_2$ and $R_3$, together with the nitrogen atom to which they are attached form a cyclic moiety that may include an additional heteroatom selected from O, S and N;

each Bx is, independently, a heterocyclic base moiety or a blocked heterocyclic base moiety; and each $R_1$ is, independently, H, a blocked hydroxyl group, a sugar substituent group or a blocked sugar substituent group;

comprising the steps of:

(a) providing a 5'-O-protected compound having one of the formulas:

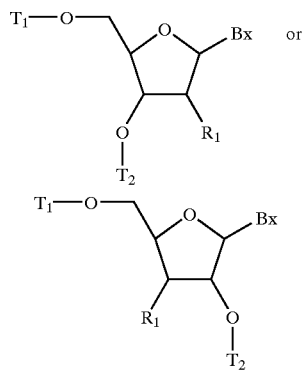

wherein:

$T_1$ is a hydroxyl protecting group; and $T_2$ is a covalent attachment to a support media, or a support media bound nucleoside, nucleotide, oligonucleoside or oligonucleotide;

(b) treating said 5'-O-protected compound with a deprotecting reagent for a time and under conditions effective to form a 5'-O-deprotected compound;

(c) coupling said 5'-O-deprotected compound with an activated phosphorus composition of the formula:

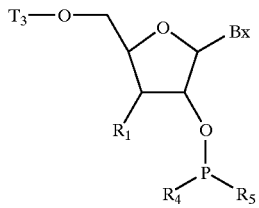

wherein:

$T_3$ is a hydroxyl protecting group, a nucleoside, a nucleotide, an oligonucleoside or an oligonucleotide; $R_4$ is $N(L_1)L_2$;

each $L_1$ and $L_2$ is, independently, $C_{1-6}$ straight or branched alkyl, or a $C_{5-7}$ cyclic aliphatic ring system;

or $L_1$ and $L_2$ are joined together to form a 4- to 13-membered heterocyclic ring system including the nitrogen atom to which $L_1$ and $L_2$ are attached, wherein said ring system optionally includes at least one additional heteroatom selected from O, N and S; and $R_5$ is $X_1$;

or $R_4$ and $R_5$ together with the phosphorus atom to which $R_4$ and $R_5$ are attached form a chiral auxiliary;

for a time and under conditions effective to form an extended compound having one of the formulas:

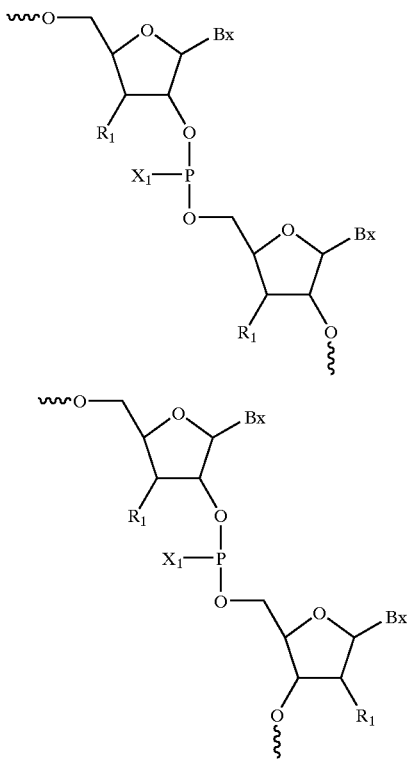

and (d) treating said extended compound with a mixture comprising an oxidizing reagent and a capping reagent for a time and under conditions effective to form said oligomeric compound.

DESCRIPTION OF PREFERRED EMBODIMENTS

The present invention is directed to methods for synthesizing oligonucleotides and analogs thereof having at least one moiety of one of the formulas:

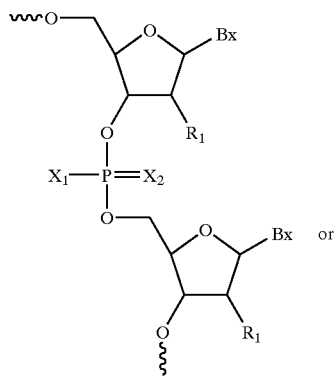

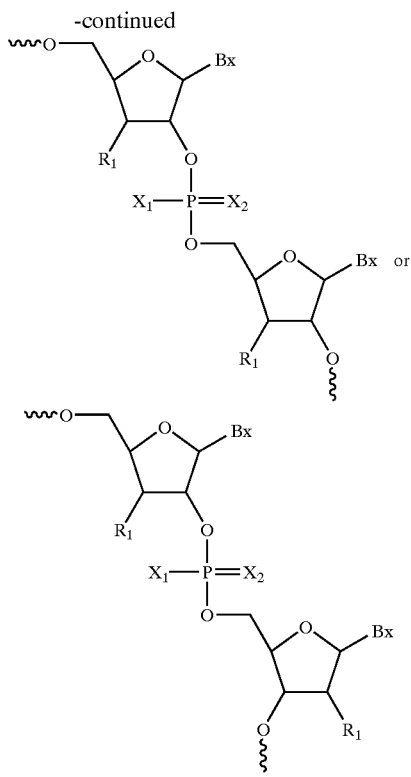

wherein:

$X_2$ is O or S;

$X_1$ is Pg—O—, Pg—S—, $C_1$-$C_{10}$ straight or branched chain alkyl, $CH_3(CH_2)_{nn}$—O—, $R_2R_3N$— or a group remaining from coupling a chiral auxiliary;

nn is from 0 to 10;

Pg is $CH_3$, —$CH_2CH_2CN$, —$C(CH_3)(CH_3)$-$CCl_3$, —$CH_2$—$CCl_3$, —$CH_2CH$=$CH_2$ $CH_2CH_2SiCH_3$, 2-yl-ethyl phenylsulfonate, δ-cyanobutenyl, cyano p-xylyl, diphenylsilylethyl, 4-nitro-2-yl-ethylbenzene, 2-yl-ethyl-methyl sulfonate, methyl-N-trifluoroacetyl ethyl, acetoxy phenoxy ethyl, or a blocking group;

each $R_2$ and $R_3$ is, independently, hydrogen, $C_1$-$C_{10}$ alkyl, cycloalkyl or aryl;

or optionally, $R_2$ and $R_3$, together with the nitrogen atom to which they are attached form a cyclic moiety that may include an additional heteroatom selected from O, S and N;

each Bx is, independently, a heterocyclic base moiety or a blocked heterocyclic base moiety; and each $R_1$ is, independently, H, a blocked hydroxyl group, a sugar substituent group, or a blocked substituent group;

The present methods can further include deblocking, deprotecting and cleaving the resulting oligomeric compound. The most common deblocked forms of $X_1$ include —OH, —SH, —N($R_2$) ($R_3$), alkyl and alkoxy groups. Purification can be performed at various stages, but is routinely performed with the terminal protecting group attached such as a trityl on purification. including protected or deprotected.

The most widely used method for the large scale synthesis of oligomeric compounds uses phosphoramidite chemistry on a support media. In general the method requires 4 separate and distinct steps per cycle: detritylation, coupling, oxidation and capping. Each step requires automated synthesis equipment time and significant quantities of reagents. In one aspect of the present invention, a method is disclosed that employs a mixture comprising an oxidizing reagent and a capping reagent to simultaneously effect oxidation of internucleoside linkages and capping of unreacted hydroxyl groups. This combined oxidation and capping step is amenable to otherwise standard synthetic methods for the synthesis of oligomeric compounds.

In general, a synthon bound to a support media, e.g. a nucleoside or nucleosidic oligomer, is extended by addition of a further synthon using standard chemistries to form a phosphite or other $P^{III}$ intermediate linkage. Treatment of this $P^{III}$ intermediate linkage in a single step with a mixture containing an oxidizing reagent and a capping reagent will give an extended compound having the desired $P^V$ oxidized linkage with unreacted hydroxyl groups capped. Advantages of the present methods can include a faster synthesis time and a reduction in cost due in part to the deletion of one of the reagent consuming steps and associated wash and rinse cycles. A further advantage can be gained by selecting an inexpensive oxidizing reagent or one that is easily prepared from inexpensive reagents.

Preferred mixtures of oxidizing and capping reagents include those that are stable and include components that are mutually soluble with each other. Oxidizing reagents amenable to the present invention should be soluble in the solution comprising the oxidizing reagent at concentrations of 0.02M, or greater, preferred about 0.1M or more, more preferred from 0.1 to 0.2M. A preferred mixture is an oxidizing reagent dissolved in cap A (20% acetic anhydride in acetonitrile) mixed with an equal volume of cap B (N-methylimidazole-pyridine-acetonitrile, 2:3:5, v/v/v). Oxidizing reagents that are soluble and stable with an equal volume mixture of cap A and cap B are preferred within the scope of the present invention.

Oxidizing reagents that are effective to transfer an oxygen atom (thereby converting a $P^{III}$ linkage to a $P^V$ linkage) include without limitation m-chloroperbenzoic acid; iodobenzene diacetate, tetra-n-butylammonium periodate; tert-butyl hydroperoxide; di-tert-butyl hydroperoxide; cumene hydroperoxide; hydrogen peroxide; bis-trimethylsilyl peroxide; and catalytic amounts of trimethylsilyl triflate; dinitrogen tetroxide and molecular oxygen in the presence of 2,2'-azobis(2-methylpropionitrile) under thermal or photochemical conditions; and (1S)-(+)-(10-camphorsulfonyl)-oxaziridine; iodine/tetrahydrofuran/water/pyridine; hydrogen peroxide/water; tert-butyl hydroperoxide; and a peracid like m-chloroperbenzoic acid (see review article Beaucage et al., *Current Protocols in Nucleic Acid Chemistry,* 2000, 3.3.1–3.3.20). In the case of oxidation to a sulfur species (sulfurization), the reaction is generally performed under anhydrous conditions with an exclusion of air, e.g. oxygen. In the case of oxidation the reaction can be performed under aqueous conditions.

Oxidizing reagents that transfer a sulfur atom (sulfurizing reagents) are used to form phosphorothioate or other sulfurized internucleoside linkages such as, for example, phosphorodithioate internucleoside linkages. Sulfurizing reagents amenable to the present invention include those that are partially or completely soluble in a selected capping reagent or reagents. In addition the sulfurizing reagent should be compatible e.g. stable and non-reactive with the capping reagents. Preferred sulfurizing reagents are commercially available in bulk for considerably less cost than most traditional sulfurizing agents that are currently in use. Alternatively, a sulfurizing reagent is selected because of its ease of synthesis from inexpensive bulk reagents.

One important criteria for a preferred sulfurizing reagent is its ability incorporate sulfur and exclude incorporation of oxygen. Analysis of an oxidized oligomer, using $^{31}P$ NMR, will give the percentages of sulfurized and oxygenized internucleoside linkages.

Preferred sulfurized linkages include those that are prepared by methods known in the art to give chirally enhanced or chirally pure sulfurized linkages for those linkages that are not achiral. Preferred sulfurized linkages that are prepared by the present methods include:

phosphorothioate (—O—P(S)(O)—O—);
phosphorodithioate (—O—P(S)(S)—O—);
phosphorthioamidate (—O—P(S)(NJ)—O—);
phosphonothioate (—O—P(J)(S)—O—);
boranothiophosphate (—O—P(S) (BJ$_3$)—J—);

wherein "J" denotes a substituent group which is commonly hydrogen or an alkyl group, but which can be a more complicated group that varies from one type of linkage to another but is well known to the art skilled.

Representative United States patents that teach the preparation of the above phosphorus atom containing linkages include, but are not limited to, U.S. Pat. Nos. 3,687,808; 4,469,863; 4,476,301; 5,023,243; 5,166,387; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,625,050; and 5,697,248, certain of which are commonly owned by the assignee of this application, and each of which is herein incorporated by reference.

Positional modifications, also known in the art, involve the linking of nucleosides in a non-naturally occurring motif. As used herein the term "positional modification" is meant to include without limitation 2',5'-internucleoside linkages. Combining modifications e.g. using modified chemistries and positional modifications of selected internucleoside linkages is also amenable to the present invention where for example a 2',5'-phosphoramidate internucleoside linkage is employed. The 2'-5'-linkage has been used at the termini of oligomeric compounds to enhance the nuclease resistance (as described in U.S. Application Serial No. 09/435,806, filed Nov. 8, 1999).

A representative list of substituent groups amenable to the present invention include $C_1$–$C_{20}$ alkyl, $C_2$–$C_{20}$ alkenyl, $C_2$–$C_{20}$ alkynyl, $C_5$–$C_{20}$ aryl, O-alkyl, O-alkenyl, O-alkynyl, O-alkylamino, (O-alkyl-N(H)alkyl ), O-alkylaminodialkyl (O-alkyl-N-(alkyl)$_2$), O-alkylalkoxy (O-alkyl-O-alkyl), O-alkyl-(N-imidazole), S-alkenyl, S-alkynyl, NH-alkyl, NH-alkenyl, NH-alkynyl, N-dialkyl, O-aryl, S-aryl, NH-aryl, O-aralkyl, S-aralkyl, NH-aralkyl, N-phthalimido, halogen (particularly fluoro), keto, carboxyl, nitro, nitroso, nitrile, trifluoromethyl, trifluoromethoxy, imidazole, azido, hydrazino, hydroxylamino, isocyanato, sulfoxide, sulfone, sulfide, disulfide, silyl, heterocycle, carbocycle, polyamine, polyamide, polyalkylene glycol, and polyethers of the formula (O-alkyl)$_m$, where m is 1 to about 10. Preferred among these polyethers are linear and cyclic polyethylene glycols (PEGs), and (PEG)-containing groups, such as crown ethers and those which are disclosed by Ouchi et al. (*Drug Design and Discovery* 1992, 9, 93), Ravasio et al. (*J. Org. Chem.* 1991, 56, 4329) and Delgardo et al. (*Critical Reviews in Therapeutic Drug Carrier Systems* 1992, 9, 249), each of which is herein incorporated by reference in its entirety. Further sugar modifications are disclosed in Cook, P.D., *Anti-Cancer Drug Design,* 1991, 6, 585–607. Fluoro, O-alkyl, O-alkylamino, O-alkyl imidazole, O-alkylaminoalkyl, and alkyl amino substitution is described in U.S. patent application Ser. No. 08/398,901, filed Mar. 6, 1995, entitled Oligomeric Compounds having Pyrimidine Nucleotide(s) with 2' and 5' Substitutions, hereby incorporated by reference in its entirety.

Additional substituent groups amenable to the present invention include —SR and —NR$_2$ groups, wherein each R is, independently, hydrogen, a protecting group or substituted or unsubstituted alkyl, alkenyl, or alkynyl. 2'-SR nucleosides are disclosed in U.S. Pat. No. 5,670,633, issued Sep. 23, 1997, hereby incorporated by reference in its entirety. The incorporation of 2'-SR monomer synthons are disclosed by Hamm et al., *J. Org. Chem.*, 1997, 62, 3415–3420. 2'-NR$_2$ nucleosides are disclosed by Goettingen, M., *J. Org. Chem.*, 1996, 61, 6273–6281; and Polushin et al., *Tetrahedron Lett.*, 1996, 37, 3227–3230.

Further substituent groups have one of formula I or II:

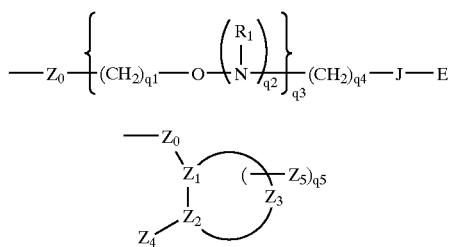

wherein:
$Z_0$ is O, S or NH;
J is a single bond, O or C(=O);
E is $C_1$–$C_{10}$ alkyl, $N(R_1)(R_2)$, $N(R_1)(R_5)$, $N=C(R_1)(R_2)$, $N=C(R_1)(R_5)$ or has one of formula III or IV;

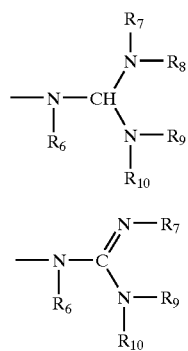

each $R_6$, $R_7$, $R_8$, $R_9$ and $R_{10}$ is, independently, hydrogen, $C(O)R_{11}$, substituted or unsubstituted $C_2$–$C_{10}$ alkyl, substituted or unsubstituted $C_2$–$C_{10}$ alkenyl, substituted or unsubstituted $C_2$–$C_{10}$ alkynyl, alkylsulfonyl, arylsulfonyl, a chemical functional group or a conjugate group, wherein the substituent groups are selected from hydroxyl, amino, alkoxy, carboxy, benzyl, phenyl, nitro, thiol, thioalkoxy, halogen, alkyl, aryl, alkenyl and alkynyl;

or optionally, $R_7$ and $R_8$, together form a phthalimido moiety with the nitrogen atom to which they are attached;

or optionally, $R_9$ and $R_{10}$, together form a phthalimido moiety with the nitrogen atom to which they are attached;

each $R_{11}$ is, independently, substituted or unsubstituted $C_1$–$C_{10}$ alkyl, trifluoromethyl, cyanoethyloxy, methoxy, ethoxy, t-butoxy, allyloxy, 9-fluorenylmethoxy, 2-(trimethylsilyl)-ethoxy, 2,2,2-trichloroethoxy, benzyloxy, butyryl, isobutyryl, phenyl or aryl;

$R_5$ is T-L,
T is a bond or a linking moiety;
L is a chemical functional group, a conjugate group or a solid support material;

each $R_1$ and $R_2$ is, independently, H, a nitrogen protecting group, substituted or unsubstituted $C_1$–$C_{10}$ alkyl, substituted or unsubstituted $C_1$–$C_{10}$ alkenyl, substituted or unsubstituted $C_2$–$C_{10}$ alkynyl, wherein said substitution is $OR_3$, $SR_3$, $NH_3^+$, $N(R_3)(R_4)$, guanidino or acyl where said acyl is an acid amide or an ester;

or $R_1$ and $R_2$, together, are a nitrogen protecting group or are joined in a ring structure that optionally includes an additional heteroatom selected from N and O;

or $R_1$, T and L, together, are a chemical functional group;

each $R_3$ and $R_4$ is, independently, H, $C_1$–$C_{10}$ alkyl, a nitrogen protecting group, or $R_3$ and $R_4$, together, are a nitrogen protecting group;

or $R_3$ and $R_4$ are joined in a ring structure that optionally includes an additional heteroatom selected from N and O;

$Z_4$ is OX, SX, or $N(X)_2$;
each X is, independently, H, $C_1$–$C_8$ alkyl, $C_1$–$C_8$ haloalkyl, C(=NH)N(H)R$_5$, C(=O)N(H)R$_5$ or OC(=O)N(H)R$_5$;

$R_5$ is H or $C_1$–$C_8$ alkyl;
$Z_1$, $Z_2$ and $Z_3$ comprise a ring system having from about 4 to about 7 carbon atoms or having from about 3 to about 6 carbon atoms and 1 or 2 hetero atoms wherein said hetero atoms are selected from oxygen, nitrogen and sulfur and wherein said ring system is aliphatic, unsaturated aliphatic, aromatic, or saturated or unsaturated heterocyclic;

$Z_5$ is alkyl or haloalkyl having 1 to about 10 carbon atoms, alkenyl having 2 to about 10 carbon atoms, alkynyl having 2 to about 10 carbon atoms, aryl having 6 to about 14 carbon atoms, $N(R_1)(R_2)$ $OR_1$, halo, $SR_1$ or CN;

each $q_1$ is, independently, an integer from 1 to 10;
each $q_2$ is, independently, 0 or 1;
$q_3$ is 0 or an integer from 1 to 10;
$q_4$ is an integer from 1 to 10;
$q_5$ is from 0, 1 or 2; and
provided that when $q_3$ is 0, $q_4$ is greater than 1.

Representative substituent groups of Formula I are disclosed in U.S. patent application Ser. No. 09/130,973, filed Aug. 7, 1998, entitled "Capped 2'-Oxyethoxy Oligonucleotides," hereby incorporated by reference in its entirety.

Representative cyclic substituent groups of Formula II are disclosed in U.S. patent application Ser. No. 09/123,108, filed Jul. 27, 1998, entitled "RNA Targeted 2'-Modified Oligonucleotides that are Conformationally Preorganized," hereby incorporated by reference in its entirety.

Particularly preferred substituent groups include O[(CH$_2$)$_n$O]$_m$CH$_3$, O(CH$_2$)$_n$OCH$_3$, O(CH$_2$)$_n$NH$_2$, O(CH$_2$)$_n$CH$_3$, O(CH$_2$)$_n$ONH$_2$, O(CH$_2$)$_n$ON[(CH$_2$)$_n$CH$_3$)]$_2$ (where n and m are from 1 to about 10), $C_1$ to $C_{10}$ lower alkyl, substituted lower alkyl, alkaryl, aralkyl, O-alkaryl or O-aralkyl, SH, SCH$_3$, OCN, Cl, Br, CN, CF$_3$ OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino and substituted silyl. Another particularly preferred modification includes 2'-methoxyethoxy (2'-O—CH$_2$CH$_2$OCH$_3$ or 2'-MOE, Martin et al., *Helv. Chim. Acta*, 1995, 78, 486). A further preferred substituent group is 2'-dimethylamino-oxyethoxy, i.e., a O(CH$_2$)$_2$ON(CH$_3$)$_2$ group, also known as 2'-DMAOE. Representative aminooxy substituent groups are described in co-owned U.S. patent application Ser. No. 09/344,260, filed Jun. 25, 1999, entitled "Aminooxy-Functionalized Oligomers"; and U.S. patent application Ser. No. 09/370,541, filed Aug. 9, 1999, entitled Aminooxy-Functionalized Oligomers and Methods for Making Same; hereby incorporated by reference in their entirety.

Other preferred modifications include 2'-methoxy (2'-O—CH$_3$), 2'-aminopropoxy (2'-OCH$_2$CH$_2$N$_2$) and 2'-fluoro (2'-F). Similar modifications may also be made at other positions on nucleosides and oligomers, particularly the 3' position of the sugar on the 3' terminal nucleoside or at a 3'-position of a nucleoside that has a linkage from the 2'-position such as a 2'-5' linked oligomer and at the 5'-position at a 5'-terminus. Oligomers may also have sugar mimetics such as cyclobutyl moieties in place of the pentofuranosyl sugar. Representative United States patents that teach the preparation of such modified sugars structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,0531 5,639,873; 5,646,265; 5,658,873; 5,670,633; and 5,700,920, certain of which are commonly owned, and each of which is herein incorporated by reference, and commonly owned U.S. patent application Ser. No. 08/468,037, filed on Jun. 5, 1995, also herein incorporated by reference.

Representative guanidino substituent groups that are shown in formula III and IV are disclosed in co-owned U.S. patent application 09/349,040, entitled "Functionalized Oligomers", filed Jul. 7, 1999, hereby incorporated by reference in its entirety.

Representative acetamido substituent groups are disclosed in U.S. patent application Ser. No. 09/378,568, entitled "2'-O-Acetamido Modified Monomers and Oligomers", filed Aug. 19, 1999, hereby incorporated by reference in its entirety.

Representative dimethylaminoethyloxyethyl substituent groups are disclosed in International Patent Application PCT/US99/17895, entitled "2'-O-Dimethylaminoethyloxyethyl-Modified Oligonucleotides", filed Aug. 6, 1999, hereby incorporated by reference in its entirety.

The use of mixed modifications in the terminal regions of an oligonucleotide to impart nuclease resistance is also within the scope of the present invention. For example an oligomeric compound of the invention can have enhanced nuclease resistance resulting from one or more modified internucleoside linkages at the 5' end and one or more substituent groups at the 3' end. Another type of a mixed modification includes having a modified internucleoside linkage and a substituent group at the same end of a selected oligomeric compound. Other examples include substituent groups or modified linkages used in conjunction with a non-standard linkage such as a 2', 5'-internucleoside linkage.

Oligomeric compounds according to the present invention preferably comprise from about 5 to about 50 nucleosides. It is more preferred that such compounds comprise from about 8 to about 30 nucleosides, with 15 to 25 nucleosides being particularly preferred.

In general, the term "hetero" denotes an atom other than carbon, preferably but not exclusively N, O, or S. Accordingly, the term "heterocyclic ring" denotes an alkyl ring system having one or more heteroatoms (i.e., non-carbon atoms). Heterocyclic ring structures of the present invention can be fully saturated, partially saturated, unsaturated or with a polycyclic heterocyclic ring each of the rings may be in any of the available states of saturation. Heterocyclic ring structures of the present invention also include heteroaryl, which includes fused systems including systems where one or more of the fused rings contain no heteroatoms. Heterocycles, including nitrogen heterocycles, according to the present invention include, but are not limited to, imidazole, pyrrole, pyrazole, indole, 1H-indazole, α-carboline, carbazole, phenothiazine, phenoxazine, tetrazole, triazole, pyrrolidine, piperidine, piperazine and morpholine groups. A more preferred group of nitrogen heterocycles includes imidazole, pyrrole, indole, and carbazole groups.

A heterocyclic base moiety (often referred to in the art simply as a "base" or a "nucleobase") amenable to the present invention includes both naturally and non-naturally occurring nucleobases. The heterocyclic base moiety further may be protected wherein one or more functionalities of the base bears a protecting group. As used herein, "unmodified" or "natural" nucleobases include the purine bases adenine and guanine, and the pyrimidine bases thymine, cytosine and uracil. Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in the *Concise Encyclopedia of Polymer Science And Engineering*, pages 858–859, Kroschwitz, J. I., ed. John Wiley & Sons, 1990, those disclosed by Englisch et al., *Angewandte Chemie, International Edition*, 1991, 30, 613, and those disclosed by Sanghvi, Y. S., Chapter 15, *Antisense Research and Applications*, pages 289–302, Crooke, S. T. and Lebleu, B., ed., CRC Press, 1993.

Certain nucleobases are particularly useful for increasing the binding affinity of oligomeric compounds. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Id., pages 276–278) and are presently preferred base substitutions, even more particularly when combined with 2'-methoxyethyl sugar modifications.

Representative United States patents that teach the preparation of modified nucleobases include, but are not limited to, U.S. Pat. Nos. 3,687,808; 4,845,205; 5,130,302; 5,134, 066; 5,175,273; 5,367,066; 5,432,272; 5,457,187; 5,459, 255; 5,484,908; 5,502,177; 5,525,711; 5,552,540; 5,587, 469; 5,594,121, 5,596,091; 5,614,617; and 5,681,941, certain of which are commonly owned, and each of which is herein incorporated by reference, and commonly owned U.S. patent application Ser. No. 08/762,488, filed on Dec. 10, 1996, also herein incorporated by reference.

The attachment of conjugate groups to oligomers is well documented in the prior art. The present methods include preparation of oligomeric compounds that include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, phospholipids, biotin, phenazine, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Representative conjugate groups are disclosed in International Patent Application PCT/US92/09196, filed Oct. 23, 1992, U.S. Pat. No. 5,578,718, issued Jul. 1, 1997, and U.S. Pat. No. 5,218,105.

Each of the foregoing is commonly assigned with this application. The entire disclosure of each is incorporated herein by reference.

Preferred conjugate groups amenable to the present invention include lipid moieties such as a cholesterol moiety (Letsinger et al., *Proc. Natl. Acad. Sci. USA*, 1989, 86, 6553), cholic acid (Manoharan et al., *Bioorg. Med. Chem. Lett.*, 1994, 4, 1053), a thioether, e.g., hexyl-S-tritylthiol (Manoharan et al., *Ann. N.Y. Acad. Sci.*, 1992, 660, 306; Manoharan et al., *Bioorg. Med. Chem. Let.*, 1993, 3, 2765), a thiocholesterol (Oberhauser et al., *Nucl. Acids Res.*, 1992, 20, 533), an aliphatic chain, e.g., dodecandiol or undecyl residues (Saison-Behmoaras et al., *EMBO J.*, 1991, 10, 111; Kabanov et al., *FEBS Lett.*, 1990, 259, 327; Svinarchuk et al., *Biochimie*, 1993, 75, 49), a phospholipid, e.g., di-hexadecyl-rac-glycerol or triethylammonium-1,2-di-O-hexadecyl-rac-glycero-3-H-phosphonate (Manoharan et al., *Tetrahedron Lett.*, 1995, 36, 3651; Shea et al., *Nucl. Acids Res.*, 1990, 18, 3777), a polyamine or a polyethylene glycol chain (Manoharan et al., *Nucleosides & Nucleotides*, 1995, 14, 969), adamantane acetic acid (Manoharan et al., *Tetrahedron Lett.*, 1995, 36, 3651), a palmityl moiety (Mishra et al., *Biochim. Biophys. Acta*, 1995, 1264, 229), or an octadecylamine or hexylamino-carbonyl-oxycholesterol moiety (Crooke et al., *J. Pharmacol. Exp. Ther.*, 1996, 277, 923).

Other groups that can be attached to oligomeric compounds to modify antisense properties include RNA cleaving complexes, pyrenes, metal chelators, porphyrins, alkylators, hybrid intercalator/ligands and photo-crosslinking agents. RNA cleavers include o-phenanthroline/Cu complexes and Ru(bipyridine)$_3^{2+}$ complexes. The Ru(bpy)$_3^{2+}$ complexes are believed to interact with nucleic acids and cleave nucleic acids photochemically. Metal chelators include EDTA, DTPA, and o-phenanthroline. Alkylators include compounds such as iodoacetamide. Porphyrins include porphine, its substituted forms, and metal complexes. Pyrenes include pyrene and other pyrene-based carboxylic acids that could be conjugated using the similar protocols.

As used herein, "polyamine" refers to a moiety containing a plurality of amine or substituted amine functionalities. Polyamines according to the present invention have at least two amine functionalities. "Polypeptide" refers to a polymer comprising a plurality of amino acids linked by peptide linkages, and includes dipeptides and tripeptides. The amino acids may be naturally-occurring or non-naturally-occurring amino acids. Polypeptides according to the present invention comprise at least two amino acids.

The methods of the present invention can employ activated phosphorus compositions in coupling reactions. As used herein, the term activated phosphorus composition includes activated phosphorus containing monomers or oligomers that are reactive with a hydroxyl group of another monomeric or oligomeric compound to form a phosphorus-containing internucleotide linkage. Such activated phosphorus groups contain activated phosphorus atoms in P$^{III}$ valence state. Such activated phosphorus atoms are known in the art and include, but are not limited to, phosphoramidite and chiral auxiliary moieties. A preferred synthesis utilizes phosphoramidites as activated phosphorus groups.

Additional activated phosphites are disclosed in Tetrahedron Report Number 309 (Beaucage and Iyer, *Tetrahedron*, 1992, 48, 2223–2311).

Representative activated phosphorus containing monomers or oligomers include those having the formula:

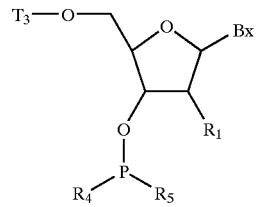

wherein each Bx is, independently, a heterocyclic base moiety or blocked heterocyclic base moiety; and each R$_1$ is, independently, H, a blocked hydroxyl group, a sugar substituent group, or a blocked substituent group;

T$_3$ is an hydroxyl protecting group, a nucleoside, a nucleotide, an oligonucleoside or an oligonucleotide;

R$_4$ is N(L$_1$)L$_2$; each L$_1$ and L$_2$ is, independently, C$_{1-6}$ straight or branched alkyl, or a C$_{5-7}$ cyclic aliphatic ring system;

or L$_1$ and L$_2$ are joined together to form a 4- to 13-membered heterocyclic ring system including the nitrogen atom to which L$_1$ and L$_2$ are attached, wherein said ring system optionally includes at least one additional heteroatom selected from O, N and S; and R$_5$ is X$_1$;

X$_1$ is Pg—O—, Pg—S—, C$_1$–C$_{10}$ straight or branched chain alkyl, CH$_3$(CH$_2$)$_{nn}$—O—, R$_2$R$_3$N— or a group remaining from coupling a chiral auxiliary;

nn is from 0 to 10;

Pg is CH$_3$, —CH$_2$CH$_2$CN, —C(CH$_3$) (CH$_3$)—CCl$_3$, —CH$_2$—CCl$_3$, —CH$_2$CH═CH$_2$ CH$_2$CH$_2$SiCH$_3$, 2-yl-ethyl phenylsulfonate, δ-cyanobutenyl, cyano p-xylyl, diphenylsilylethyl, 4-nitro-2-yl-ethylbenzene, 2-yl-ethyl-methyl sulfonate, methyl-N-trifluoroacetyl ethyl, acetoxy phenoxy ethyl, or a blocking group;

each R$_2$ and R$_3$ is, independently, hydrogen, C$_1$–C$_{10}$ alkyl, cycloalkyl or aryl;

or optionally, R$_2$ and R$_3$, together with the nitrogen atom to which they are attached form a cyclic moiety that may include an additional heteroatom selected from O, S and N; or R$_4$ and R$_5$ together with the phosphorus atom to which R$_4$ and R$_5$ are attached form a chiral auxiliary.

Groups that are attached to the phosphorus atom of internucleotide linkages before and after oxidation (R$_4$ and R$_5$) can include nitrogen containing cyclic moieties such as morpholine. Such oxidized internucleoside linkages include a phosphoromorpholidothioate linkage (Wilk et al., *Nucleosides and nucleotides*, 1991, 10, 319–322). Further cyclic moieties amenable to the present invention include mono-, bi- or tricyclic ring moieties which may be substituted with groups such as oxo, acyl, alkoxy, alkoxycarbonyl, alkyl, alkenyl, alkynyl, amino, amido, azido, aryl, heteroaryl, carboxylic acid, cyano, guanidino, halo, haloalkyl, haloalkoxy, hydrazino, ODMT, alkylsulfonyl, nitro, sulfide, sulfone, sulfonamide, thiol and thioalkoxy. A preferred bicyclic ring structure that includes nitrogen is phthalimido.

Some representative examples of R$_4$ and R$_5$ groups which are known to the art skilled and are amenable to the present invention are shown below:

| R₄ | R₅ | R₄ | R₅ |
|---|---|---|---|
| 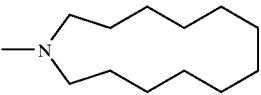 | —O—CH₃ | —N—(CH₃)₂ | 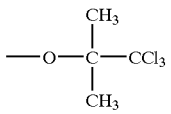 |
| 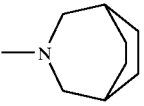 | —O—CH₃ | —N—(CH₂CH₃)₂ | 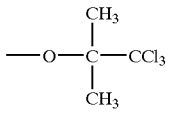 |
| 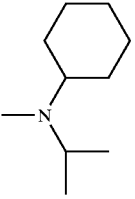 | —O—CH₃ | —N—[CHCH₃ \| CH₃]₂ | 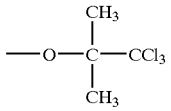 |
| 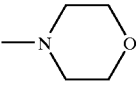 | 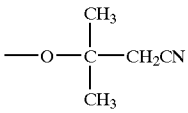 | 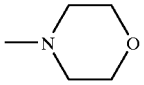 | 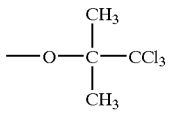 |
| —N—[CHCH₃ \| CH₃]₂ | —O—CH₂CH₂SiCH₃ | —N—(CH₃)₂ | —O—CH₂—CCl₃ |
| —N—[CHCH₃ \| CH₃]₂ | 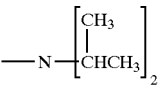 | —N—[CHCH₃ \| CH₃]₂ | —O—CH₂CH=CH₂ |
further examples include:
| R₄ | R₅ | R₄ | R₅ |
|---|---|---|---|
| —N—(CH₃)₂ | 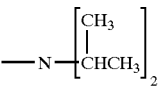 | 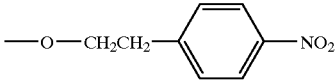 | —O—CH₃ |
| 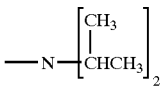 | 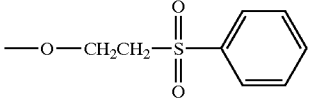 | 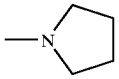 | —O—CH₃ |
| 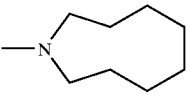 | 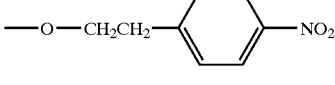 | 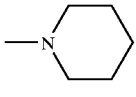 | —O—CH₃ |
| 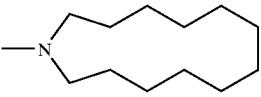 | 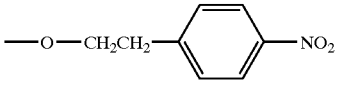 | 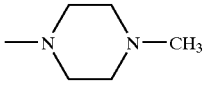 | —O—CH₃ |

-continued

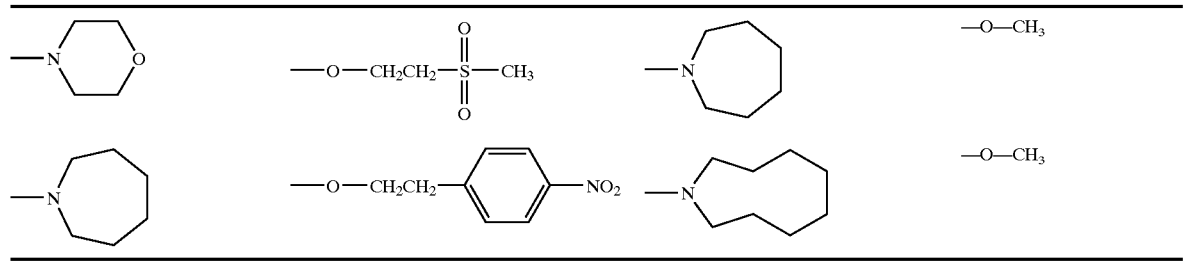

Functional groups including substituent groups discussed above which may be located on heterocyclic base and sugar moieties are routinely blocked with protecting (blocking groups) during synthesis and subsequently deblocked. In general, a blocking group renders a chemical functionality of a molecule inert to specific reaction conditions and can later be removed from such functionality in a molecule without substantially damaging the remainder of the molecule. See, Green and Wuts, Protective Groups in Organic Synthesis, 2d edition, John Wiley & Sons, New York, 1991. For example, amino groups can be blocked with nitrogen protecting groups such as phthalimido, 9-fluorenylmethoxycarbonyl (FMOC), triphenylmethylsulfenyl, t-BOC or benzyl groups. Carboxyl groups can be protected as acetyl groups. Representative hydroxyl protecting groups are described by Beaucage et al., *Tetrahedron* 1992, 48, 2223. Preferred hydroxyl protecting groups are acid-labile groups, such as the trityl, monomethoxytrityl, dimethoxytrityl, trimethoxytrityl, 9-phenylxanthin-9-yl (Pixyl) and 9-(p-methoxyphenyl) xanthin-9-yl (MOX). Chemical functional groups can also be "blocked" by including them in a precursor form. Thus an azido group can be considered a "blocked" form of an amine as the azido group is easily converted to the amine. Further representative protecting groups utilized in oligonucleotide synthesis are discussed in Agrawal et al., Protocols for Oligonucleotide Conjugates, Eds., Humana Press, New Jersey, 1994, Vol. 26, pp. 1–72.

Standard oligonucleotide synthesis using phosphite ($P^{III}$) chemistry involves treatment of the growing oligomer with a deprotecting reagent to create a free hydroxyl position that is available for a further coupling reaction. Hydroxyl protecting groups are preferably removed using a weak acid. Dependant on the choice of protecting group the deprotecting reagent can be acidic, basic, neutral or fluoride mediated. A representative list of deprotecting reagents amenable to the present methods includes without limitation protic acids used for removing acid labile protecting groups such as dichloro- and trichloroacetic acids, Lewis acids such as $BF_3$-etherate, zinc bromide, $AlCl_1$, $TiCl_4$, (Et)AlCl, (I-Bu)$_2$AlCl and other reagents such as ceric ammonium nitrate, 1,1,1,3,3,3-hexafluoro-2-propanol, and diethyloxomalonate. A preferred deprotecting reagent that is used routinely for example for the removal of various trityl protecting groups is 2–5% dichloroacetic acid in either dichloromethane or dichloroethane.

The use of blocking groups is common practice to protect or block reactive or functional groups that are typically located on or linked to nucleobases, internucleotide linkages and sugars. Generally, blocking groups are removed using conditions that are stronger than those encountered during the iterative elongation steps in oligomer synthesis. This allows for deprotection of hydroxyl groups and coupling without effecting blocked positions. As used herein, the term "blocking group" describes a group that is stable to the conditions that are used to deprotect groups such as hydroxyl groups during the iterative elongation steps of oligomeric compound synthesis. Blocking groups are generally removed after the desired length has been synthesized. Standard phosphoramidite chemistry frequently uses acid labile protecting groups on hydroxyls that are used for coupling steps and strong base labile blocking groups to block other reactive positions not used in coupling steps. Many examples of protecting and blocking groups are collectively described in for example Green and Wuts ibid. Preferred blocking groups are removed by treatment with base. Some representative base labile protecting groups include without limitation, Fmoc (E. Atherton and R. C. Sheppard in The Peptides, S. Udenfriend, J. Meienhofer, Eds., Academic Press, Orlando, 1987, volume 9, p.1), and various substituted sulfonylethyl carbamates exemplified by the Nsc group (Samukov et al., *Tetrahedron Lett,* 1994, 35:7821; Verhart and Tesser, *Rec. Trav. Chim. Pays-Bas,* 1987, 107:621).

After synthesis the resulting oligomeric compound generally is cleaved from the solid support to obtain the free oligomer. The step of deprotecting the blocked 5'-O-hydroxyl is usually performed separately as this is generally accomplished using an acidic deblocking reagent. This step is routinely performed after deprotection, cleavage and purification has been performed to enhance the purification process by keeping the terminal hydroxyl blocked. The deprotection and cleavage steps can be separated into separate steps or combined into a single step depending on the particular protecting groups, solid support linking groups and the choice of reagent or reagents used. In a preferred embodiment the simultaneous deprotection and cleavage of the final oligomeric compound following synthesis is accomplished in one step using a solution of ammonium hydroxide ($NH_4OH$ (30%) for 15 hours at 60° C., filtered, rinsed with ethanol/water (1/1, v/v), the combined solutions are evaporated to dryness under vacuum).

The purification of oligomeric compounds is generally by reversed phase high performance liquid chromatography (RP-HPLC) performed on a Waters Nova-Pak C18 column (3.9×300 mm) using a Waters HPLC system (600E System Controller, 996 Photodiode Array Detector, 717 Autosampler). For analysis an acetonitrile (A)/0.1M triethylammonium acetate gradient is used: 5% to 35% A from 0 to 10 min, then 35% to 40% A from 10 to 20 min, then 40% to 95% A from 20 to 25 min, flow rate=10 mL/min/50% A from 8 to 9 min, 9 to 26 min at 50%, flow rate=1.0 mL/min, tR(DMT-off) 10–11 min, tR(DMT-on) 14–16 min. The DMT-on fractions are collected and are evaporated in vacuum, redissolved in water and the DMT group removed as described below.

Removal of the final hydroxyl protecting group from the 5'hydroxyl group is generally performed by treatment with an acidic solution such as acetic acid. The oligomeric compound is treated with the acidic solution for about 30 minutes at room temperature. The mixture is further treated with sodium acetate and cold ethanol followed by vortexing and cooling with dry ice. The precipitate is centrifuged, separated, washed and dried to give the final deprotected product.

The term "nucleoside" as used in connection with this invention refers to a monomeric unit made up of a heterocyclic base moiety joined to a sugar moiety or sugar mimetic through a glycosyl linkage. The term "nucleotide" refers to a nucleoside having a phosphate group on its 3' or 5' sugar hydroxyl group.

In the context of this invention, the terms "oligomer" and "oligomeric compound" refer to a plurality of naturally-occurring or non-naturally-occurring nucleosides joined together in a specific sequence. The terms "oligomer" and "oligomeric compound" include oligonucleotides, oligonucleotide analogs, oligonucleosides and chimeric oligomeric compounds where there are more than one type of internucleoside linkages dividing the oligomeric compound into regions. Whereas the term "oligonucleotide" has a well defined meaning in the art, the term "oligomeric compound" or "oligomer" is intended to be broader, inclusive of oligomers having all manner of modifications known in the art. Gapped or chimeric compounds are disclosed in for example, U.S. Pat. No. 5,623,065, issued Apr. 22, 1997, the contents of which are incorporated herein by reference.

As used herein, the term "oligonucleoside" includes oligomers or polymers containing two or more nucleoside subunits having a non-phosphodiester linking moiety. Oligonucleosides according to the invention have a ribofuranose moiety attached to a nucleobase through a glycosyl bond.

Gapmer technology has been developed to incorporate modifications at the ends ("wings") of oligomeric compounds, leaving a phosphorothioate gap in the middle for RNase H activation (Cook, P. D., *Anti-Cancer Drug Des.*, 1991, 6, 585–607; Monia et al., *J. Biol. Chem.*, 1993, 268, 14514–14522). In a recent report, the activities of a series of uniformly 2'-O modified 20 mer RNase H-independent oligonucleotides that were antisense to the 5'-cap region of human ICAM-1 transcript in HUVEC cells, were compared to the parent 2'-deoxy phosphorothioate oligonucleotide (Baker et al., *J. Bio. Chem.*, 1997, 272, 11994–12000). The 2'-MOE/P=O oligomer demonstrated the greatest activity with an $IC_{50}$ of 2.1 nM ($T_m$=87.1° C.), while the parent P=S oligonucleotide analog had an $IC_{50}$ of 6.5 nM ($T_m$=79.2° C.). Correlation of activity with binding affinity is not always observed as the 2'-F/P=S ($T_m$=87.9° C.) was less active than the 2'-MOE/P=S ($T_m$=79.2° C.) by four fold. The RNase H competent 2'-deoxy P=S parent oligonucleotide exhibited an $IC_{50}$=41 nM.

As used herein the term "chiral auxiliary" is meant to include groups that function to provide chirality to internucleoside phosphorus linkages during synthesis. Chiral auxiliaries amenable to the present invention include those that form a $P^{III}$ intermediate capable of being oxidized. Chiral auxiliaries will give either Sp or Rp chirality for the respective internucleoside linkage in the final oligomeric compound. Accordingly, chiral auxiliaries are allowed to remain on the growing chain, and are removed at the end of the iterative synthetic regime. Removal of chiral auxiliaries can be conveniently accomplished in a single treatment after the completion of the iterative synthesis. Chiral auxiliaries and methods of their incorporation using standard protocols are disclosed in commonly owned U.S. patent application Ser. No. 09/438,989, filed on Nov. 12, 1999, incorporated herein by reference. Further chiral auxiliaries have been previously reported for use in the preparation of oligomeric phosphorothioates (see Iyer et al., *Tetrahedron letters*, 1998, 39, 2491–2494 and Wilk et al., *J. Am. Chem. Soc.*, 2000, 122, 2149–2156). Representative chiral auxiliaries include, without limitation those having the following formulas:

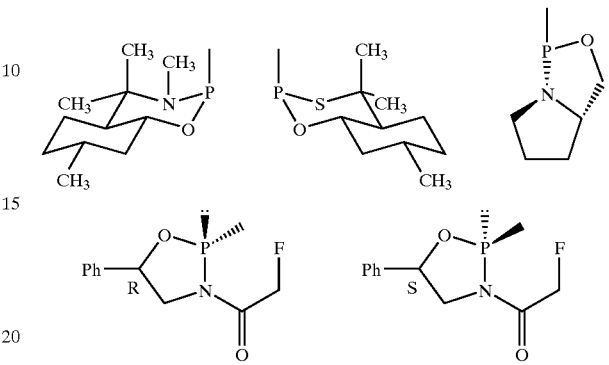

As used herein, the term "alkyl" includes, but is not limited to, straight chain, branched chain and alicyclic hydrocarbon groups. Alkyl groups of the present invention may be substituted. Representative alkyl substituents are disclosed in U.S. Pat. No. 5,212,295, at column 12, lines 41–50, hereby incorporated by reference in its entirety. Substituent groups include, but are not limited to, alkyl, alkenyl, alkynyl, aryl, hydroxyl, alkoxy, alcohol, benzyl, phenyl, nitro, thiol, thioalkoxy, thioalkyl, trifluoromethyl, halo, nitrile, trifluoromethoxy and azido. As used herein, the term "lower alkyl" is intended to mean an alkyl group having 10 or fewer carbons.

Alkenyl groups according to the invention are to straight chain, branch chain, and cyclic hydrocarbon groups containing at least one carbon-carbon double bond, and alkynyl groups are to straight chain, branch chain, and cyclic hydrocarbon groups containing at least one carbon-carbon triply bond. Alkenyl and alkynyl groups of the present invention can be substituted.

Aryl groups are substituted and unsubstituted aromatic cyclic moieties including but not limited to phenyl, naphthyl, anthracyl, phenanthryl, pyrenyl, and xylyl groups. Alkaryl groups are those in which an aryl moiety links an alkyl moiety to a core structure, and aralkyl groups are those in which an alkyl moiety links an aryl moiety to a core structure.

As used herein, the term "aralkyl" denotes alkyl groups which bear aryl groups, for example, benzyl groups. The term "alkaryl" denotes aryl groups which bear alkyl groups, for example, methylphenyl groups. As used herein, the term "aryl" denotes aromatic cyclic groups including, but not limited to, phenyl, naphthyl, anthracyl, phenanthryl and pyrenyl. Preferred aryl and aralkyl groups include, but are not limited to, phenyl, benzyl, xylyl, naphthyl, toluyl, pyrenyl, anthracyl, azulyl, phenethyl, cinnamyl, benzhydryl, and mesityl. Typical substituents for substitution include, but are not limited to, hydroxyl, alkoxy, alcohol, benzyl, phenyl, nitro, thiol, thioalkoxy, halogen, or alkyl, aryl, alkenyl, or alkynyl groups.

As used herein, the term "alkanoyl" has its accustomed meaning as a group of formula —C(=O)-alkyl. A preferred alkanoyl group is the acetyl group.

In one aspect of the present invention oligomeric compounds are prepared using support bound methodologies wherein the oxidation and capping steps are combined into a single step. A first modified or unmodified nucleoside is attached to a support media preferably via a linkage to the 3'-position. The nucleoside could alternatively be attached to a support media through the 2'-position as when preparing positionally modified internucleoside linkages. Alternatively, the support media with the desired nucleoside attached can be purchased from a number of commercial sources. In a traditional synthesis this nucleoside will ultimately become the nucleoside at the 3'-end of the final oligomeric compound. The support media with the nucleoside attached is placed in a reaction vessel such as a glass reactor. One of the hydroxyl groups (preferably the 5'-hydroxyl group) is deprotected and treated with a second nucleoside having a group reactive with the hydroxyl group such as an activated phosphorus group or a chiral auxiliary. This coupling step is preferably performed in the presence of an activating agent such as DBU or 1-H-tetrazole. The linkage thus formed is treated with a mixture containing reagents for oxidizing and capping. A preferred mixture for incorporating a sulfur atom is (0.3M) dimethylthiuram disulfide in cap A (20% acetic anhydride in acetonitrile) mixed with and equal volume of cap B (20% N-methylimidazole, 30% pyridine and 50% aetonitrile, by volume). The cycle is optionally repeated to add additional nucleosides until the desired oligomeric compound is completed.

As used herein, the term "sulfurizing reagent" includes without limitation, dimethylthiuram disulfide (Cummings et al., *Ind. Eng. Chem.*, 1928, 20, 1173); 1,2,4-dithiazolidine-3,5-dione (DTSNH, see Xu et al., *Nucleic Acids Research*, 1996, 24, 1602–1607); 3-methyl-1,2,4-dithiazolin-5-one (MEDITH, see Zang et al., *Tetrahedron Lett.*, 1999, 40, 2095–20980); phenylacetyl disulfide (PADS, see Kamer et al., *Tetrahedron Lett.*, 1989, 30, 6757–6760; Cheruvallath et al., *Organic Process Research & Development*, 2000, 4, 199–204); tetraethylthiuram disulfide (TETD, see Vu et al., *Tetrahedron Lett.*, 1991, 32, 3005–3008); 3H-1,2-benzodithiol-3-one-1,1-dioxide (Beaucage reagent, see e.g. Iyer, R. P., et.al., *J. Chem. Soc.*, 1990, 112, 1253–1254, and Iyer, R. P., et.al., *J. Org. Chem.*, 1990, 55, 4693–4699); tetraethylthiuram disulfide (see e.g., Vu, H., Hirschbein, B. L., *Tetrahedron Lett.*, 1991, 32, 3005–3008); dibenzoyl tetrasulfide (see e.g., Rao, M. V., et.al., *Tetrahedron Lett.*, 1992, 33, 4839–4842); benzyltriethylammonium tetrathiomolybdate (BTTM, see e.g., Rao, M. V., et.al., *Tetrahedron Lett.*, 1994, 35, 6741–6744); di(phenylacetyl)disulfide (see e.g., Kamer, P. C. J., *Tetrahedron Lett.*, 1989, 30, 6757–6760); Bis(O,O-diisopropoxy phosphinothioyl) disulfides (see Stec et al., *Tetrahedron Lett.*, 1993, 34, 5317–5320); 3-ethoxy-1,2,4-dithiazoline-5-one (EDITH, see Xu et al., *Nucleic Acids Research*, 1996 24, 1602–1607, and *Nucleic Acids Research*, 1996 24, 3643–3644); Bis(p-chlorobenzenesulfonyl)disulfide (see *Nucleic Acids Research*, 1995 23, 4029–4033); bis(ethoxythiocarbonyl)-tetrasulfide (see Zang et al., *Tetrahedron Lett.*, 1998, 39, 2467–2470); bis(p-toluenesulfonyl)disulfide (Efimov et al., *Nucleic Acids Res.*, 1995, 23, 4029–4033); 3-amino-1,2,4-dithiazole-5-thione (see *Org. Process Res. Dev.*, 2000, 4, 194–198); ethylthiuram disulfide CAS #3082-38-0; 5,6-dihydro-3H-imidazo[2,1-C]-1,2,4-dithiazole-3-thione CAS #33813-20-6; 4-methyl-5-(methylimino)-1,2,4-dithiazolidine-3-thione CAS #20042-85-7; sulfur, sulfur in combination with ligands like triaryl, trialkyl, triaralkyl, or trialkaryl phosphines. The foregoing references are hereby incorporated by reference in their entirety.

A preferred list of sulfurizing reagents includes: 3-amino-1,2,4-dithiazole-5-thione; 3-ethoxy-1,2,4-dithiazoline-5-one; 1,2,4-dithiazolidine-3,5-dione; 3-methyl-1,2,4-dithiazolin-5-one; and dimethylthiuram disulfide.

A representative list of capping reagents useful in the methods of the present invention include without limitation, acetic anhydride, t-butylphenoxyacetic anhydride, phosphite monoesters, and selected acid chlorides preferably delivered concurrently with a nucleophilic catalyst (e.g. a strong base) such as for example N-methylimidazole or triethylamine. Generally capping reagents comprise a mixture of Cap A and Cap B. Representative mixtures include without limitation:

Cap A: acetic anhydride in acetonitrile or tetrahydrofuran;
chloroacetic anhydride in acetonitrile or tetrahydrofuran;
Cap B: N-methylimidazole and pyridine in acetonitrile or tetrahydrofuran;
    4-dimethylaminopyridine (DMAP) and pyridine in acetonitrile or tetrahydrofuran;
    2,6-lutidine and N-methylimidazole in acetonitrile or tetrahydrofuran.

A more detailed description capping reagents is discussed in U.S. Pat. No. 4,816,571, issued Mar. 28, 1989 which is incorporated herein by reference. A preferred capping reagent is acetic anhydride routinely used as a mixture of cap A and cap B.

During the coupling step one compound having an active phosphate is coupled to a second compound having a free hydroxyl group. An activating agent is not believed to be essential for this step but one is generally used to increase the reaction efficiency. A list of activators and references for each can be found in Eleueri et al., *Organic Process Research & Development*, 2000, 4, 182–189. Preferred activators include without limitation: 1H-tetrazole, 5-(2-nitrophenyl)-1H-tetrazole, 5-(p-nitrophenyl)-1H-tetrazole, 5-trifluoromethyl-1H-tetrazole, 5-ethylthio-1H-tetrazole, 5-benzyltio-1H-tetrazole, 2,4,5-tribromoimidazole, 2-nitroimidazole, 4,5-dichloroimidazole, 2-bromo-4,5-dicyanoimidazole, 4,5-dicyanoimidazole, N-methylimidazole hydrochloride, 1-hydroxybenzotriazole, 5-chlorobenzotriazole, chlorotrimethylsilane, benzimidazolium triflate, imidazolium triflate, pyridinium hydrochloride/imidazole, pyridinium tetrafluoroborate, pyridinium chloride, pyridinium bromide, pyridinium 4-methylbenzinesulfonate, N-methylimidazolium trifluroborate, N-methylanilinium trichloroacetate, N-methylanilinium trifluoroacetate, 1H-tetrazole/DMAP, 1H-tetrazole/N-methylimidazole, and N-methylimidazolium trifluoromethanesulfonate (see see review article Beaucage et al., *Current Protocols in Nucleic Acid Chemistry*, 2000, 3.3.1–3.3.20).

The current method of choice for the preparation of oligomeric compounds uses support media. Support media is used to attach a first nucleoside or larger nucleosidic synthon which is then iteratively elongated to give a final oligomeric compound. Support media can be selected to be insoluble or have variable solubility in different solvents to allow the growing oligomer to be kept out of or in solution as desired. Traditional solid supports are insoluble and are routinely placed in a reaction vessel while reagents and solvents react and or wash the growing chain until cleavage frees the final oligomer. More recent approaches have introduced soluble supports including soluble polymer supports to allow precipitating and dissolving the bound oligomer at desired points in the synthesis (Gravert et al., *Chem. Rev.*, 1997, 97, 489–510). Representative support media that are amenable to the methods of the present invention include without limitation: controlled pore glass (CPG); oxalyl-controlled pore glass (see, e.g., Alul, et al., *Nucleic Acids Research* 1991, 19, 1527); TENTAGEL Support, (see, e.g., Wright, et al., *Tetrahedron Letters* 1993, 34, 3373); or POROS, a copolymer of polystyrene/divinylbenzene available from Perceptive Biosystems. The use of a soluble support media, poly(ethylene glycol), with molecular weights between 5 and 20 kDa, for large-scale synthesis of phosphorothioate oligonucleotides is described in, Bonora et al., *Organic Process Research & Development*, 2000, 4, 225–231.

It was previously reported (Cummings A. D. et al. Ind. Eng. Chem., 1928, 20, 1173) that dimethylthiuram disulfide was not a stable compound and decomposes slowly on standing. The dimethylthiuram disulfide, after standing for 1 month, failed to show a melting point of 102° C. The decomposition products were identified as hydrogen sulfide, elemental sulfur and methyl isothiocyanate. The lack of long shelf life for dimethylthiuram disulfide has been attributed to the dithiocabamate derivative of methylamine, which is a primary amine. The present invention provides a new and improved procedure for the synthesis of dimethylthiuram disulfide (see Example 7) which utilizes an acid wash at the end of the synthesis. The primary amine is protonated which stabilizes the dithiocarbamate structure from degradation. A further improvement was realized by oxidizing the intermediate with hydrogen peroxide as opposed to iodine. This led to the preparation of white crystalline product instead of the yellow unstable product previously reported. Dimethylthiuram disulfide made by this protocol is very stable even after six months of storage at room temperature.

Oligomeric compounds prepared by the methods of the present invention can be used in diagnostics, therapeutics and as research reagents and kits. They can also be used in pharmaceutical compositions by including a suitable pharmaceutically acceptable diluent or carrier. They can further be used for treating organisms having a disease characterized by the undesired production of a protein. For this purpose, the organism is contacted with an oligomer having a sequence that is capable of specifically hybridizing with a strand of nucleic acid encoding the undesirable protein. Treatments of this type can be practiced on a variety of organisms ranging from unicellular prokaryotic and eukaryotic organisms to multicellular eukaryotic organisms. Any organism that utilizes DNA-RNA transcription or RNA-protein translation as a fundamental part of its hereditary, metabolic or cellular control is susceptible to therapeutic and/or prophylactic treatment in accordance with the invention. Seemingly diverse organisms such as bacteria, yeast, protozoa, algae, all plants and all higher animal forms, including warm-blooded animals, can be treated. Further, each cell of multicellular eukaryotes can be treated, as they include both DNA-RNA transcription and RNA-protein translation as integral parts of their cellular activity. Furthermore, many of the organelles (e.g., mitochondria and chloroplasts) of eukaryotic cells also include transcription and translation mechanisms. Thus, single cells, cellular populations or organelles can also be included within the definition of organisms that can be treated with therapeutic or diagnostic oligomeric compounds of the invention.

Those skilled in the art will appreciate that numerous changes and modifications may be made to the preferred embodiments of the invention and that such changes and modifications may be made without departing from the spirit of the invention. It is, therefore, intended that the appended claims cover all such equivalent variations as fall within the true spirit and scope of the invention.

EXAMPLE 1

5c-Methyl-2t [(1-methyl-1-methylamino) ethyl]-cyclohexan-1r-ol (Compound 1)

The title compound is synthesized according to a literature procedure using (+)-pulegone (He et al., *J. Org. Chem.*, 1990, 55, 2114–2119) by first preparing 5c-Methyl-2t [(1-methyl-1-benzylamino) ethyl]-cyclohexan-1r-ol. This compound is subjected to hydrogenolysis by Pd/H$_2$ to give the corresponding amino alcohol (removal of benzyl group). The amino alcohol is then treated with 1 equivalent of HCHO followed by NaCNBH$_3$ reduction to give the title Compound. This isomer is used to prepare Rp phosphorothioate linkages.

The isomer of the title compound (Compound 2) is prepared from the naturally occuring (−)-pulegone (available from Fluka), Compound 2 is obtained as a Chiral Adjuvant following a literature procedure (He et al., Tetrahedron, 1987, 43, 4979-4987). This isomer is used to prepare Sp phosphorothioate linkages.

EXAMPLE 2

Preparation of Sp Monomer (Compound 3)

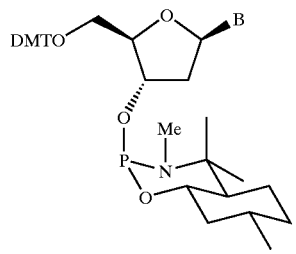

Compound 2 is treated with PCl$_3$ (1 equivalent) with excess of Hunig base in THF solvent at −50° C. for 10 minutes. The resulting chloro compound is treated with a selected 2'-deoxy-5-O-DMT-nucleoside having a free 3'-OH group (2'-O-deoxy-5'-O-DMT-6-N-benzoyl adenosine, 2'-O-deoxy-5'-O-DMT-4-N-benzoyl cytodine, 2'-O-deoxy-5'-O-DMT-2-N-butyryl guanosine, 2'-O-deoxy-5'-O-DMT-thymidine or modified optionally protected 5-O-DMT-nucleoside). TLC and $^{13}$C NMR analysis is used to reveal the formation of a single diastereomer. The crude material is washed with saturated sodium bicarbonate and dried over anhydrous sodium sulfate. The resulting material is purified either by crystallization or by silica gel column chromatography.

EXAMPLE 3

Protected Dimer, (Compound 4)

Purified compound 3 is condensed with a 5'-HO-T-CPG (Example 5), or other solid support bound 5'-OH-nucleoside (such as 2'-O-deoxy-6-N-benzoyl adenosine, 2'-O-deoxy-4-N-benzoyl cytidine, 2'-O-deoxy-2-N-isobutyryl guanosine or other modified optionally protected 5'-OH'-3'-CPG-nucleoside), for 2 hours using tetrazole as the coupling agent. The capping and sulfurization is completed in one step using (0.3M) dimethylthiuram disulfide in cap A (20% acetic anhydride in acetonitrile) mixed with and equal volume of cap B (20% N-methylimidazole, 30% pyridine and 50% aetonitrile, by volume) giving the protected phosphorothioate dimer attached to solid support. The protected dimer is cleaved from the solid support, deprotected by treatment with concentrated ammonium hydroxide (30%, 12 hours), and purified purified by HPLC. The nucleoside dimer is treated with 80% aqueous acetic acid to remove the 5'-triyl group. The Sp configuration is assigned as described below in the procedures.

EXAMPLE 4

Preparation of Rp Monomer (Compound 5)

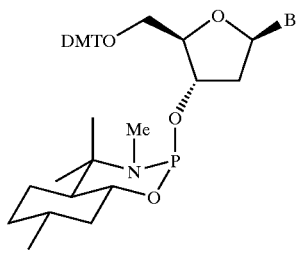

The Rp monomer is prepared following the procedures illustrated for the Sp dimer in example 2 using Compound 1.

EXAMPLE 5

Preparation of Rp Dimer (Compound 6)

The Rp dimer is prepared following the procedures illustrated for the Sp dimer in example 3 using Compound 5.

EXAMPLE 6

Synthesis of Chirally pure 5'-$T_{Sp}T_{Rp}T_{Rp}T_{Rp}T_{Rp}T_{Sp}$T-3' Phosphorothioate Heptamer 50 milligram (2 μmole) of 5'-O-dimethoxytritylthymidine bound to CPG (controlled pore glass) through an ester linkage is taken up in a glass reactor, and a toluene solution of 3% dichloroacetic acid (v/v) is added to deprotect the 5'-hydroxyl group. The product is washed with acetonitrile and a 0.2 M solution of Compound 3 (B=T) in acetonitrile (25 fold excess) and a 0.5 M solution of DBU in acetonitrile (200 fold excess) is added and allowed to react at room temperature for 15 minutes. The product is washed with acetonitrile followed by the addition of a solution of (0.3M) dimethylthiuram disulfide in cap A (20% acetic anhydride in acetonitrile) mixed with and equal volume of cap B (20% N-methylimidazole, 30% pyridine and 50% aetonitrile, by volume) with reaction allowed to progress at room temperature for 5 minutes. The product is washed with acetonitrile.

In the next cycle Compound 5 (B=T) is used as the incoming monomer and the cycle is repeated. This complete cycle is repeated four more times to introduce the Rp linkages. In the final cycle Compound 3 is used as the incoming monomer which introduces the terminal Sp linkage. The solid support containing the heptamer is treated with 30% aqueous ammonium hydroxide solution for 90 minutes at room temperature. The aqueous solution is filtered, and concentrated under reduced pressure to give the chirally pure phosphorothioate heptamer.

EXAMPLE 7

Preparation of Dimethylthiuram Disulfide

In a 4-litter bottle equipped with a mechanical stirrer, sodium hydroxide (80 g, 2 mol) was dissolved in water (500 mL) and the solution was cooled to 0° C. (ice-water bath). THF (200 mL), methylamine (40% in water, 170 mL, 2 mol) and carbon disulfide (120 mL, 2 mol) were added and the mixture as stirred at 0° C. for 30 minutes. Crushed ice (1.5 kg) was added, followed by glacial acetic acid (300 mL). Hydrogen peroxide (30%, 100 mL, 1 mol) was added dropwise over 10 minutes with temperature maintained below 50° C. by adding ice with stirring. Hexanes (or heptane) (800 mL) was added and the mixture was stirred for another 30 minutes in an ice-water bath. The mixture was filtered and washed with aqueous trichloroacetic acid (2%, 5×200 mL) and hexanes (or heptane) (2×200 mL). The product was dried in air for 1 day to a constant weight to give an off-white solid (205.8, yield: 97%). M.p. 98–100° C. (dec.)

HPLC analysis: Column: YMC ODS-AQ S3 120A, 4.6× 100 mm Flow rate: 1.0 mL/min Detector: UV at 244 nm Sample: inject 10 μL (1–2 mg in 1 mL of glacial acetic acid) Retention time: 5.4 min

| Linear gradient | | |
|---|---|---|
| Time (Min) | Acetonitrile | 0.2% Acetic acid |
| 0 | 50 | 50 |
| 15 | 90 | 10 |
| 25 | 90 | 10 |
| 30 | 50 | 50 |
| 35 | 50 | 50 |

The crude product (200g) was recrystallized by dissolution in THF (1L) containing trichloroacetic acid (10 g). Water (200 mL) was added followed by slow addition of hexanes (5 L) over 30 minutes. After stirring at 0° C. for 1 hour, filtering, washing with 2% aqueous trichloroacetic acid (3×200 mL) followed by drying the recrystallized dimethylthiuram disulfide was obtained.

EXAMPLE 8

Sulfurization of Triethyl Phosphite with Various Sulfurizing Reagents

Small scale sulfurization reactions were performed in NMR tubes using $CD_3CN$ to measure the efficiency of various sulfurization reagents. The basic reaction scheme is shown below:

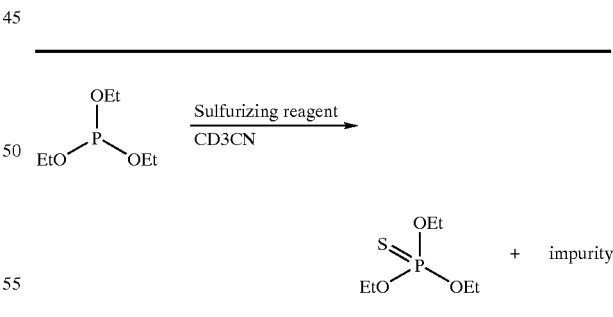

| Reagent (=S) | % P=O | % product | % product (w/tetrazole) |
|---|---|---|---|
| Beaucage | 0.7 | 100 | — |
| Phenylacetyl disulfide | 0.7 | 100 | — |
| Tetraethylthiuram disulfide | 2 | 82 | 100 |
| Tetramethylthiuram disulfide | 4 | 2 | 93 |
| Morpholino thiocarbonyl disulfide | 1.7 | 50 | 93 |
| Dimethylthiuram disulfide | 0 | 100 | 100 |

The experimental conditions varied dependent on the sulfurizing reagent used. The conditions are detailed below:

1. 0.5 M beaucage in CD$_3$CN (1 mL) and triethyl phosphite (17 μL) for 5 min.

2. 0.2 M PADS in 3-picoline-CD$_3$CN (1:1, 1 mL) and triethyl phosphite (17 μL) for 5 min.

3. 0.2 M tetraethylthiuram disulfide in CD$_3$CN (1 mL) and triethyl phosphite (17 μL) for 5 min.

4. 0.2 M tetraethylthiuram disulfide and 0.3 M tetrazole in CD$_3$CN (1 mL) and triethyl phosphite (17 μL) for 5 min.

EXAMPLE 9

Solid Phase Synthesis of Full Phosphorothioate 5'-TTTTTTTC-3' Using Tetraethylthiuram Disufide The above sequence was synthesized following standard phosphoramidite protocols. The 4-step procedure was performed on via automated synthesis using a 6.3 mL column on an OligoPilot II (Armersham Pharmacia). The reagents and the amounts used are as follows:

1. Detritylation: 3% dichloroacetic acid in dichloromethane.

2. Coupling: 2 equivalents of phosphoramidite for 5 min.

3. Thiolation: 1 column volume (CV) 0.5 M tetraethylthiuram disulfide and 0.45 M tetrazole in acetonitrile for 10 min.

4. Capping: 0.5 CV of cap A (20% acetic anhydride in acetonitrile) and cap B (N-methylimidazole-pyridine-acetonitrile, 2:3:5, v/v/v) for 1 min.

After synthesis, the solid support was heated with concentrated aqueous ammonia solution (50 mL) at 58° C. overnight and the filtered. The filtrate was concentrated under reduced pressure and dried. The $^{31}$P NMR study showed 3.7% P=O and 96.3% P=S.

EXAMPLE 10

Solid Phase Synthesis of Full Phosphorothioate 5'-TTTTTTTC-3' Using Morpholino Thiocarbonyl Disulfide The above sequence was synthesized following standard phosphoramidite protocols. The 4-step procedure was performed on via automated synthesis using a 6.3 mL column on an OligoPilot II (Armersham Pharmacia). The reagents and the amounts used are as follows:

1. Detritylation: 3% dichloroacetic acid in dichloromethane.

2. Coupling: 2 equivalents of phosphoramidite for 5 min.

3. Thiolation: 1 column volume (CV) 0.3M morpholino thiocarbonyl disulfide and 0.23M tetrazole in dichloromethane-acetonitrile (1:1 v/v) for 10 min.

4. Capping: 0.5 CV of cap A (20% acetic anhydride in acetonitrile) and cap B (N-methylimidazole-pyridine-acetonitrile, 2:3:5, v/v/v) for 1 min.

After synthesis, the solid support was heated with concentrated aqueous ammonia solution (50 mL) at 58° C. overnight and the filtered. The filtrate was concentrated under reduced pressure and dried. LP NMR showed 3.3% P=O and 96.7% P=S.

EXAMPLE 11

Solid Phase Synthesis of Full Phosphorothioate 20 mer, SEQ ID NO. 1 (5'-GTGCTCATGG TGCACGGTCT-3'; all C's are 5-Me-C's)

A. Using Phenylacetyl Disulfide (PADS)

The above sequence (SEQ ID NO. 1) was synthesized following standard phosphoramidite protocols. The 4-step procedure was performed on via automated synthesis using a 6.3 mL column on an OligoPilot II (Armersham Pharmacia). The reagents and the amounts used are as follows:

1. Detritylation: 3t dichloroacetic acid in dichloromethane.

2. Coupling: 2 equivalents of phosphoramidite for 5 min.

3. Thiolation: 1 column volume (CV) 0.2 M phenylacetyl disulfide (PADS) in 3-picoline-acetonitrile (1:1 v/v) for 10 min.

4. Capping: 0.5 CV of cap A (20% acetic anhydride in acetonitrile) and cap B (N-methylimidazole-pyridine-acetonitrile, 2:3:5, v/v/v) for 1 min.

After synthesis, the solid support was heated with concentrated aqueous ammonia solution (50 mL) at 58° C. overnight and the filtered. The filtrate was concentrated under reduced pressure and dried. Purity and $^{31}$P NMR data are shown below.

B. Using Dimethylthiuram Disulfide

The above sequence (SEQ ID NO. 1) was synthesized following standard phosphoramidite protocols. The 3-step procedure was performed on via automated synthesis using a 6.3 mL column on an OligoPilot II (Armersham Pharmacia).

1. Detritylation: 3% dichloroacetic acid in dichloromethane.

2. Coupling: 2 equivalents of phosphoramidite for 5 min.

3. Thiolation-capping: 1 column volume (CV) 0.3 M dimethylthiuram disulfide (DMDS) in cap A (20% acetic anhydride in acetonitrile) and 1CV cap B (N-methylimidazole-pyridine-acetonitrile, 2:3:5, v/v/v) for 1 min.

After synthesis, the solid support was heated with concentrated aqueous ammonia solution (50 mL) at 58° C. overnight and the filtered. The filtrate was concentrated under reduced pressure and dried. Purity and $^{31}$P NMR data are shown below.

| Rgt | Loading | Crude O.D. | O.D./mmol | % Trityl-on | % CGE | % P=O |
|---|---|---|---|---|---|---|
| PADS | 173 | 25625 | 148 | 74.7 | 78.1 | 0.40 |
| DMDS | 169 | 26265 | 149 | 76.2 | 81.5 | 0.22. |

EXAMPLE 12

Preparation of Thymidine 8-mer Having Phosphodiester Internucleotide Linkages Using a Single Step Combining Oxidation and Capping (5'-TTTTTTTT-3')

A thymidine 8-mer was prepared following the procedures illustrated above (see example 11). The synthesis was performed as per the 3-step procedure (combined oxidation and capping steps) using a 6.3 mL column on an OligoPilot II (Armersham Pharmacia) and 1.89 g Primer Support T (93 μmol/g).

1. Detritylation: 3% dichloroacetic acid in toluene.

2. Coupling: 3 equivalents of phosphoramidite for 5 min.

3. Oxidation-capping: 1 CV of 0.1 M iodine in cap A (20% acetic anhydride in acetonitrile) and 1 CV of cap B (N-methylimidazole-pyridine-acetonitrile, 2:3:5, v/v/v) for 2 min.

After synthesis, the solid support was heated with concentrated aqueous ammonia solution (50 mL) at 58° C. overnight and the filtered. The filtrate was concentrated under reduced pressure prior to analysis.

Crude yield: 7564 O.D.; full length percentage: 90.1%; $^{31}$P NMR: −0.383, −0.276 and −0.215 ppm.

What is claimed is:

1. A method of preparing an oligomeric compound having at least one moiety of formula:

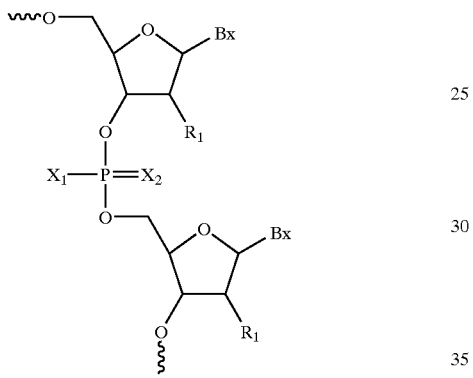

wherein:

$X_2$ is O or S;

$X_1$ is Pg—O—, Pg—S—, $C_1$–$C_{10}$ straight or branched chain alkyl, $CH_3(CH_2)_{nn}$—O—, $R_2R_3N$— or a group remaining from coupling a chiral auxiliary:

nn is from 0 to 10;

Pg is $CH_3$, —$CH_2CH_2CN$, —$C(CH_3)(CH_3)$—$CCl_3$, —$CH_2$—$CCl_3$, —$CH_2CH$=$CH_2$, $CH_2CH_2SiCH_3$, 2-yl-ethyl phenylsulfonate, δ-cyanobutenyl, cyano p-xylyl, diphenylsilylethyl, 4-nitro-2-yl-ethylbenzene, 2-yl-ethyl-methyl sulfonate, methyl-N-trifluoroacetyl ethyl, acetoxy phenoxy ethyl, or a blocking group;

$R_1$ is, independently, hydrogen, a blocked hydroxyl group, or a sugar substituent group;

$R_2$ is, independently, hydrogen, a $C_1$–$C_{10}$ alkyl, a cycloalkyl, or aryl;

$R_3$ is, independently, hydrogen, a $C_1$–$C_{10}$ alkyl, a cycloalkyl, or aryl;

$R_4$ is, independently, $N(L_1)L_2$;

or optionally, $R_2$ and $R_3$, together with the nitrogen atom to which they are attached form a cyclic moiety;

each Bx is, independently, a heterocyclic base moiety; and comprising the steps of:

(a) providing a 5'-O-protected compound of the formula:

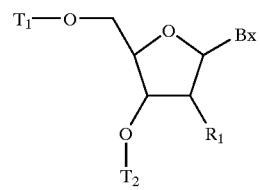

wherein:

$T_1$ is a hydroxyl protecting group; and $T_2$ is a covalent attachment to a support media, a nucleoside bound to a support media, a nucleotide, an oligonucleoside or an oligonucleotide;

(b) treating said 5'-O-protected compound with a deprotecting reagent for a time and under conditions effective to form a 5'-deprotected compound;

(c) coupling said 5'-O-deprotected compound with an activated phosphorus composition of the formula:

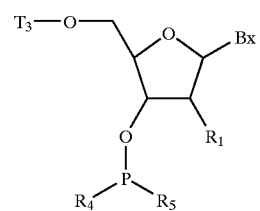

wherein:

$T_3$ is a hydroxyl protecting group, a nucleoside, nucleotide, an oligonucleoside or an oligonucleotide;

each $L_1$ and $L_2$ is, independently, $C_{1-6}$ straight or branched alkyl, or a $C_{5-7}$ cyclic aliphatic ring system;

or $L_1$ and $L_2$ are joined together to form a 4- to 13-membered heterocyclic ring system including the nitrogen atom to which $L_1$ and $L_2$ are attached; and $R_5$ is $X_1$;

or $R_4$ and $R_5$ together with the phosphorus atom to which $R_4$ and $R_5$ are attached form a chiral auxiliary;

for a time and under conditions effective to form an extended compound having the formula:

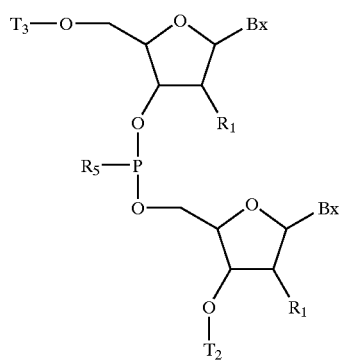

(d) treating said extended compound with a mixture comprising an oxidizing reagent and a capping reagent in a single step and for a time and under conditions effective to form said oligomeric compound, and (e) treating said oligomeric compound with a reagent for a time and under conditions effective to remove said blocking groups thereby forming a deblocked oligomeric compound.

2. The method of claim 1 wherein said reagent in step (e) is effective to cleave the oligomeric compound from the support media.

3. The method of claim 2 wherein said reagent in step (e) is aqueous ammonium hydroxide.

4. The method of claim 1 further comprising treating said oligomeric compound with a further reagent for a time and under conditions effective to cleave the oligomeric compound from the support media.

5. The method of claim 1 further comprising treating said oligomeric compound with a deprotecting reagent for a time and under conditions effective to deprotect the $T_3$ hydroxyl protecting group.

6. The method of claim 1 wherein said mixture comprises from 0.02M to 0.2M oxidizing reagent.

7. The method of claim 6 wherein said mixture comprises from 0.1M to 0.2M oxidizing reagent.

8. The method of claim 1 wherein said oxidizing reagent transfers an oxygen atom.

9. The method of claim 8 wherein said oxidizing reagent is iodine, m-chloroperbenzoic acid, iodobenzene diacetate, tetra-n-butylammonium periodate, tert-butyl hydroperoxide, di-tert-butyl hydroperoxide, cumene hydroperoxide, hydrogen peroxide; bis-trimethylsilyl peroxide; dinitrogen tetroxide, oxone, molecular oxygen, (1S)-(+)(10-camphorsulfonyl)oxaziridine or a peracid.

10. The method of claim 9 wherein said oxidizing reagent is iodine, m-chloroperbenzoic acid, iodobenzene diacetate, tert-butyl hydroperoxide, di-tert-butyl hydroperoxide, hydrogen peroxide, oxone, molecular oxygen or a peracid.

11. The method of claim 1 wherein said oxidizing reagent transfers a sulfur atom.

12. The method of claim 11 wherein said oxidizing reagent is 3-amino-1,2,4-dithiazole-5-thione; 3-ethoxy-1,2,4-dithiazoline-5-one; 1,2,4-dithiazolidine-3,5-dione; 3-methyl-1,2,4-dithiazolin-5-one; or dimethylthiuram disulfide.

13. The method of claim 12 wherein said oxidizing reagent is dimethylthiuram disulfide.

14. The method of claim 1 wherein said capping reagent comprises about one part by volume of either acetic anhydride in acetonitrile or tetrahydrofuran; or chloroacetic anhydride in acetonitrile or tetrahydrofuran; added to about one part by volume of either N-methylimidazole and pyridine in acetonitrile or tetrahydrofuran; or t-butylphenoxyacetic anhydride in acetonitrile or tetrahydrofuran.

15. The method of claim 14 wherein said capping reagent comprises about one part by volume of 20% acetic anhydride in acetonitrile mixed with about one part by volume of a solution having 20% N-methylimidazole, 30% pyridine and 50% acetonitrile.

16. The method of claim 1 wherein said mixture comprises dimethylthiuram disulfide, acetic anhydride, acetonitrile, N-methyl imidazole and pyridine.

17. The method of claim 1 wherein said mixture comprises from about 0.05M to 0.2M dimethylthiuram disulfide, about 10% acetic anhydride, about 10% N-methyl imidazole and about 15% pyridine in a suitable solvent.

18. The method of claim 17 wherein said solvent is acetonitrile, toluene, ethyl acetate, tetrahydrofuran, dichloromethane, dichloroethane, dioxane, dimethylacetamide and dimethylformamide.

19. The method of claim 1 wherein said coupling of the 5'-O-deprotected compound with the activated phosphorus composition is performed in the presence of an activating agent.

20. The method of claim 19 wherein said activating agent is 1-H-tetrazole or 4,5 dicyanoimidazole.

21. The method of claim 1 where said cyclic moiety is morpholino or phthalimido.

22. The method of claim 1 wherein each $L_1$ and $L_2$ is $C_{1-6}$alkyl.

23. The method of claim 22 wherein each $L_1$ and $L_2$ is isopropyl.

24. The method of claim 1 wherein $L_1$ and $L_2$ are joined together to form a heterocyclic ring system including the nitrogen atom to which said $L_1$ and $L_2$ are attached, wherein said ring system optionally includes at least one additional heteroatom selected from O, N and S.

25. The method of claim 24 wherein said heterocyclic ring system is morpholino.

26. The method of claim 1 wherein each of said sugar substituent groups is, independently, $C_1$–$C_{20}$ alkyl, $C_2$–$C_{20}$ alkenyl, $C_2$–$C_{20}$ alkynyl, $C_5$–$C_{20}$ aryl, O-alkyl, O-alkenyl, O-alkynyl, O-aryl, O-aralkyl, O-alkylamino, O-alkylaminoalkyl (O-alkyl-N(H)alkyl), O-alkylaminodialkyl (O-alkyl-N-(alkyl)$_2$), O-alkylalkoxy (O-alkyl-O-alkyl), O-alkyl-(N-imidazole), thiol, S-alkyl, S-alkenyl, S-alkynyl, NH-alkyl, NH-alkenyl, NH-alkynyl, N-dialkyl, S-aryl, NH-aryl, S-aralkyl, NH-aralkyl, N-phthalimido, halogen keto, carboxyl, nitro, nitroso, nitrile, trifluoromethyl, trifluoromethoxy, N-imidazole, azido, hydrazino, hydroxylamino, isocyanato, sulfoxide, sulfone, sulfide, disulfide, silyl, heterocycle, carbocycle, polyamine, polyamide, polyalkylene glycol, or polyether;

or, alternatively, one or more substituent groups has one of formula I or II:

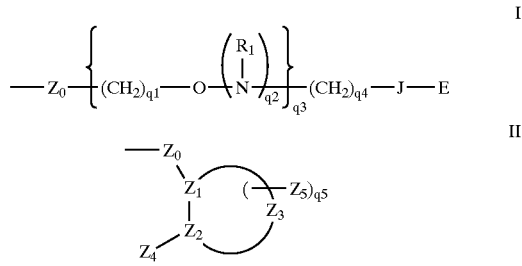

wherein $Z_0$ is O, S or NH;

J is a single bond, O or C(=O);

E is $C_1$–$C_{10}$ alkyl, N($R_1$)($R_2$), N($R_1$)($R_5$), N=C($R_1$)($R_2$), N=C($R_1$)($R_5$) or has one of formula III or IV;

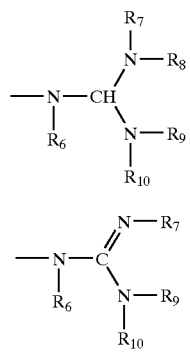

each $R_6$, $R_7$, $R_8$, $R_9$ and $R_{10}$ is, independently, hydrogen, $C(O)R_{11}$, substituted or unsubstituted $C_1$–$C_{10}$ alkyl, substituted or unsubstituted $C_2$–$C_{10}$ alkenyl, substituted or unsubstituted $C_2$–$C_{10}$ alkynyl, alkylsulfonyl, arylsulfonyl, a chemical functional group or a conjugate group, wherein the substituent groups are selected from hydroxyl, amino, alkoxy, carboxy, benzyl, phenyl, nitro, thiol, thioalkoxy, halogen, alkyl, aryl, alkenyl and alkynyl;

or optionally, $R_7$ and $R_8$, together form a phthalimido moiety with the nitrogen atom to which they are attached;

or optionally, $R_9$ and $R_{10}$, together form a phthalimido moiety with the nitrogen atom to which they are attached;

each $R_{11}$ is, independently, substituted or unsubstituted $C_1$–$C_{10}$ alkyl, trifluoromethyl, cyanoethyloxy, methoxy, ethoxy, t-butoxy, allyloxy, 9-fluorenylmethoxy, 2-(trimethylsilyl)-ethoxy, 2,2,2-trichloroethoxy, benzyloxy, butyryl, iso-butyryl, phenyl or aryl;

$R_{5'}$ is T-L,

T is a bond or a linking moiety;

L is a chemical functional group, a conjugate group or a support media;

each $R_{1'}$ and $R_{2'}$ is, independently, H, a nitrogen protecting group, substituted or unsubstituted $C_1$–$C_{10}$ alkyl, substituted or unsubstituted $C_2$–$C_{10}$ alkenyl, substituted or unsubstituted $C_2$–$C_{10}$ alkynyl, wherein said substitution is $OR_3$, $SR_3$, $NH_3^+$, $N(R_3)(R_4)$, guanidino or acyl where said acyl is an acid amide or an ester;

or $R_{1'}$ and $R_{2'}$, together, are a nitrogen protecting group or are joined in a ring structure that optionally includes an additional heteroatom selected from N and O;

or $R_{1'}$, T and L, together, are a chemical functional group;

each $R_{3'}$ and $R_{4'}$ is, independently, H, $C_1$–$C_{10}$ alkyl, a nitrogen protecting group, or $R_{3'}$ and $R_{4'}$, together, are a nitrogen protecting group;

or $R_{3'}$ and $R_{4'}$ are joined in a ring structure that optionally includes an additional heteroatom selected from N and O;

$Z_4$ is OX, SX, or $N(X)_2$;

each X is, independently, H, $C_1$–$C_8$ alkyl, $C_1$–$C_8$ haloalkyl, $C(=NH)N(H)R_{5'}$, $C(=O)N(H)R_{5'}$ or $OC(=O)N(H)R_{5'}$;

$R_{5'}$ is H or $C_1$–$C_8$ alkyl;

$Z_1$, $Z_2$ and $Z_3$ comprise a ring system having from about 4 to about 7 carbon atoms or having from about 3 to about 6 carbon atoms and 1 or 2 hetero atoms wherein said hetero atoms are selected from oxygen, nitrogen and sulfur and wherein said ring system is aliphatic, unsaturated aliphatic, aromatic, or saturated or unsaturated heterocyclic;

$Z_5$ is alkyl or haloalkyl having 1 to about 10 carbon atoms, alkenyl having 2 to about 10 carbon atoms, alkynyl having 2 to about 10 carbon atoms, aryl having 6 to about 14 carbon atoms, $N(R_{1'})(R_{2'})$ $OR_{1'}$, halo, $SR_{1'}$ or CN;

each $q_1$ is, independently, an integer from 1 to 10;

each $q_2$ is, independently, 0 or 1;

$q_3$ is 0 or an integer from 1 to 10;

$q_4$ is an integer from 1 to 10;

$q_5$ is from 0, 1 or 2; and provided that when $q_3$ is 0, $q_4$ is greater than 1.

27. The method of claim 1 wherein said $X_1$ is Pg—O—, Pg—S—, $CH_3$—, $CH_3$—O—, morpholino or $R_2R_3N$— where each $R_2$ and $R_3$ is, independently, hydrogen or $C_1$–$C_{10}$ alkyl.

28. The method of claim 1 wherein said Pg is $CH_2CH_2CN$, diphenylsilylethyl, δ-cyanobutenyl, cyano p-xylyl, methyl-N-trifluoroacetyl ethyl or acetoxy phenoxy ethyl.

29. The method of claim 1 wherein said heterocyclic base moiety is adenine, $N^6$-benzoyladenine, cytosine, $N^4$-benzoylcytosine, 5-methylcytosine, $N^4$-benzoyl-5-methylcytosine, thymine, uracil, guanine, $N^2$-isobutyrylguanine or 2-aminoadenine.

30. The method of claim 1 wherein said support media bound nucleoside, nucleotide, oligonucleoside or oligonucleotide is blocked at reactive sites.

31. The method of claim 1 wherein said blocking groups are acid stable.

32. The method of claim 1 wherein said blocking groups are base labile.

33. The method of claim 1 wherein said deprotecting reagent is acidic, neutral or basic.

34. The method of claim 33 wherein said deprotecting reagent is dichloroacetic acid, trichloracetic acid, zinc bromide, $AlCl_3$, $TiCl_4$, (Et)AlCl, (i-Bu)$_2$AlCl, ceric ammonium nitrate, 1,1,1,3,3,3-hexafluoro-2-propanol or diethyloxomalonate.

35. The method of claim 34 wherein said deprotecting reagent is 2–5% dichloroacetic acid in dichloromethane or dichloroethane.

36. The method of claim 1 wherein said deprotecting reagent is a fluoride moiety.

37. The method of claim 36 wherein said fluoride moiety is $BF_3$-etherate.

38. The method of claim 1 wherein said oligomeric compound comprises from 5 to about 50 nucleosides.

39. The method of claim 1 wherein said oligomeric compound comprises from 8 to about 30 nucleosides.

40. The method of claim 1 wherein said oligomeric compound comprises from 15 to about 25 nucleosides.

* * * * *

UNITED STATES PATENT AND TRADEMARK OFFICE
CERTIFICATE OF CORRECTION

PATENT NO. : 6,809,195 B1  Page 1 of 1
APPLICATION NO. : 09/640279
DATED : October 26, 2004
INVENTOR(S) : Yogesh S. Sanghvi et al.

It is certified that error appears in the above-identified patent and that said Letters Patent is hereby corrected as shown below:

Column 37, Claim 1, line 54, please delete "a $C_1$-$C_{10}$ alkyl, a" and insert therefor -- $C_1$-$C_{10}$ alkyl, --;

Column 37, Claim 1, line 56, please delete "a $C_1$-$C_{10}$ alkyl, a" and insert therefor -- $C_1$-$C_{10}$ alkyl, --;

Column 38, Claim 1, line 35, please delete "5'-deprotected" and insert therefor -- 5'-O-deprotected --;

Column 38, Claim 1, line 50, please insert -- a -- after "nucleoside";

Column 39, Claim 10, lines 47, please delete "(1S)-(+)(10-" and insert therefor -- (1S)-(+)-(10- --;

Column 40, Claim 26, lines 66-67, please delete "$N(R_1)(R_2)$, $N(R_1)(R_5)$, $N=C(R_1)(R_2)$, $N=C(R_1)(R_5)$" and insert therefor
-- $N(R_{1'})(R_{2'})$, $N(R_{1'})(R_{5'})$, $N=C(R_{1'})(R_{2'})$, $N=C(R_{1'})(R_{5'})$ --;

Column 42, Claim 34, line 44, please delete "trichloracetic" and insert therefor -- trichloroacetic --.

Signed and Sealed this

Eighteenth Day of March, 2008

JON W. DUDAS
*Director of the United States Patent and Trademark Office*